United States Patent
Duyk et al.

(10) Patent No.: US 6,531,644 B1
(45) Date of Patent: Mar. 11, 2003

(54) METHODS FOR IDENTIFYING ANTI-CANCER DRUG TARGETS

(75) Inventors: Geoffrey Duyk, Hillsborough, CA (US); Felix D. Karim, Menlo Park, CA (US); Casey Kopczynski, Belmont, CA (US); Jenny Kopczynski, Belmont, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 09/488,495

(22) Filed: Jan. 20, 2000

Related U.S. Application Data

(60) Provisional application No. 60/176,372, filed on Jan. 14, 2000.

(51) Int. Cl.[7] .............................................. G01N 33/00
(52) U.S. Cl. ................................ 800/3; 800/8; 800/13
(58) Field of Search ............................. 800/3, 8, 9, 13; 424/9.2

(56) References Cited

FOREIGN PATENT DOCUMENTS

| WO | WO95/14085 | 5/1995 |
| WO | WO 99/01763 | * 1/1999 |
| WO | WO99/24603 | 5/1999 |

OTHER PUBLICATIONS

Seamark, Progress and Emerging Problems in Li vestock Transgenesis: a Summary Perspective, 1994, Reprod.Fertil. Dev. vol. 6:653–657.*
Wall, Transgenic Livestock: Progress and Prospects for the Future, 1996; Theriogenology 45:57–68.*
Moread.ith et. al., Gene targeting in embryonic stem celllls: the new physiology and metabolism, 1997; J. Mol. Med75: 208–216.*
Houdebine, Production of pharmaceutical proteins from transgenic animals, 1994; Journal of Biotechnology 34: 269–287.*
Karim et.al.; A Screen for Genes That Function Downstream of Ras 1 During Drosophila Eye Development, 1996, Genetics 143: 315–329.*
Qin et.al.; Deregulated transcription factor E2F–1 expression leads to S–phase entry and p53–mediated apoptosis, 1994, Proc. Natl. Acad. Sci. , vol. 91: 10918–10922.*
Vooijs et.al.; Flp–mediated tissue–specific inactivation of the retinoblastoma tumor suppressor gene in the mouse, 1998, Oncogene 17: 1–12.*
Greenhalgh et.al.; Paradoxical Tumor Inhibitory Effect of p53 Loss in Transgenic Mice Expressing Epidermal–targeted v–ras, v–fos, or Human Transforming Growthj Factor, 1996, Cancer Research 56: 4413–4423.*
Dobrowolski; An E2F dominant negative mutant blocks EIA induced cell cycle progression, 1994, Oncogene 9: 2605–2612.*

Sharp; RNAi and double–strand RNA, 1999, Genes & Development 13: 139–141.*
Tuschl et.al.; Targeted mRNA degradation by double–stranded RNA in vitro, 1999, Genes & Development 13: 3191–3197.*
Zhao et.al.; Double–Stranded RNA Injection Produces Non-specific Defects in Zebrafish, 2001, Developmental Biology 229: 215–223.*
Wargelius et.al.; Double–Stranded RNA Induces Specific Developmental Defects in Zebrafish Embryos, 1999, Biochemical and Biophysical Research Communications 262: 156–161.*
Oates et.al.; Too Much Interference: Injection of Double–Stranded RNA Has Nonspecific Effects in the Zebrafish Embryo, 2000, Developmental Biology 224: 20–28.*
Caplen et.al.; dsRNA–mediated gene suilencing in cu.ltured Drosophila cells: a tissue culture model for the analysis of RNA interference, 2000, Gene 252: 91–105.*
Montgomery et.al.; Double–stranded RNA as a mediator in sequence–specific genetic silencing and co–suppression, 1998, TIG vol. 14: 255–257.*
Doye V. and Hurt E.C., "Genetic Approaches to Nuclear Pore Structure and Function," Trends in Genetics, 1995, 11:235–241.
Hartwell L.H., et al., "Integrating Genetic Approaches Into the Discovery of Anticancer Drugs," Science, 1997, 278:1064–1068.
St John M.A.R., and Xu T., "Insights From Model Systems: Understanding Human Cancer in a Fly?," Am. J. Hum. Genet., 1997, 61:1006–1010.

* cited by examiner

*Primary Examiner*—James Ketter
*Assistant Examiner*—Richard Schnizer
(74) *Attorney, Agent, or Firm*—Laleh Shayesteh; Jan Brunelle

(57) ABSTRACT

Methods, transformation constructs, and transgenic animals for identifying anti-tumor agents and anti-tumor drug targets are described. The transformation constructs are used to generate transgenic animals that have altered expression of an oncogene or tumor suppressor gene in a target tissue that is dispensable for viability and reproduction. In some embodiments, the altered expression results in abnormal proliferation of the target tissue and normal proliferation in all other tissues. Anti-tumor drug targets can be identified by generating progeny of the transgenic animals that have mutations in various genes. Gene mutations that result in a specific reduction or killing of the target tissue are identified as possible anti-tumor drug targets and are further evaluated. Anti-tumor agents are identified that mimic the effect of the gene mutations that result in specific reduction of the target tissue. Alternatively, anti-tumor agents can be identified by administering various compounds directly to the transgenic animals, or their progeny, and selecting as putative therapeutic agents, compounds that result in target-tissue specific antiproliferation.

23 Claims, 12 Drawing Sheets

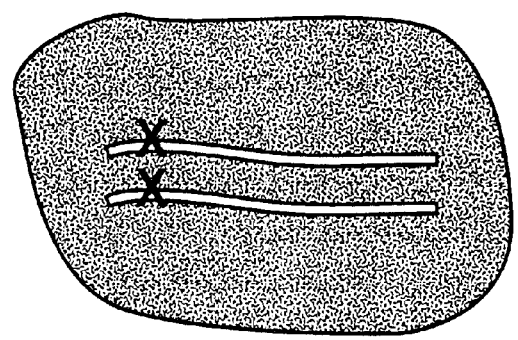
FIG._1A
Cell with Altered Proliferation
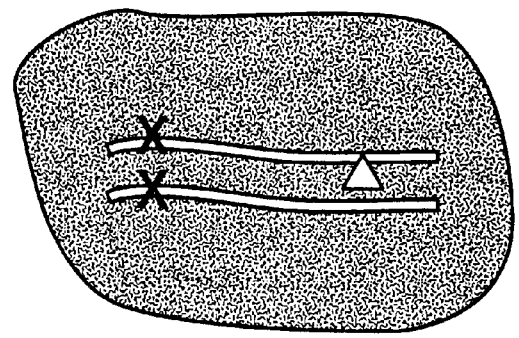
FIG._1B
Cell Death
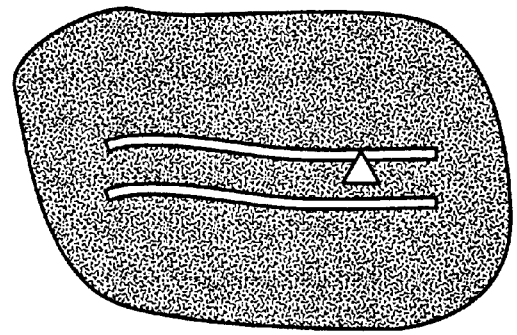
FIG._1C
Viable Cell

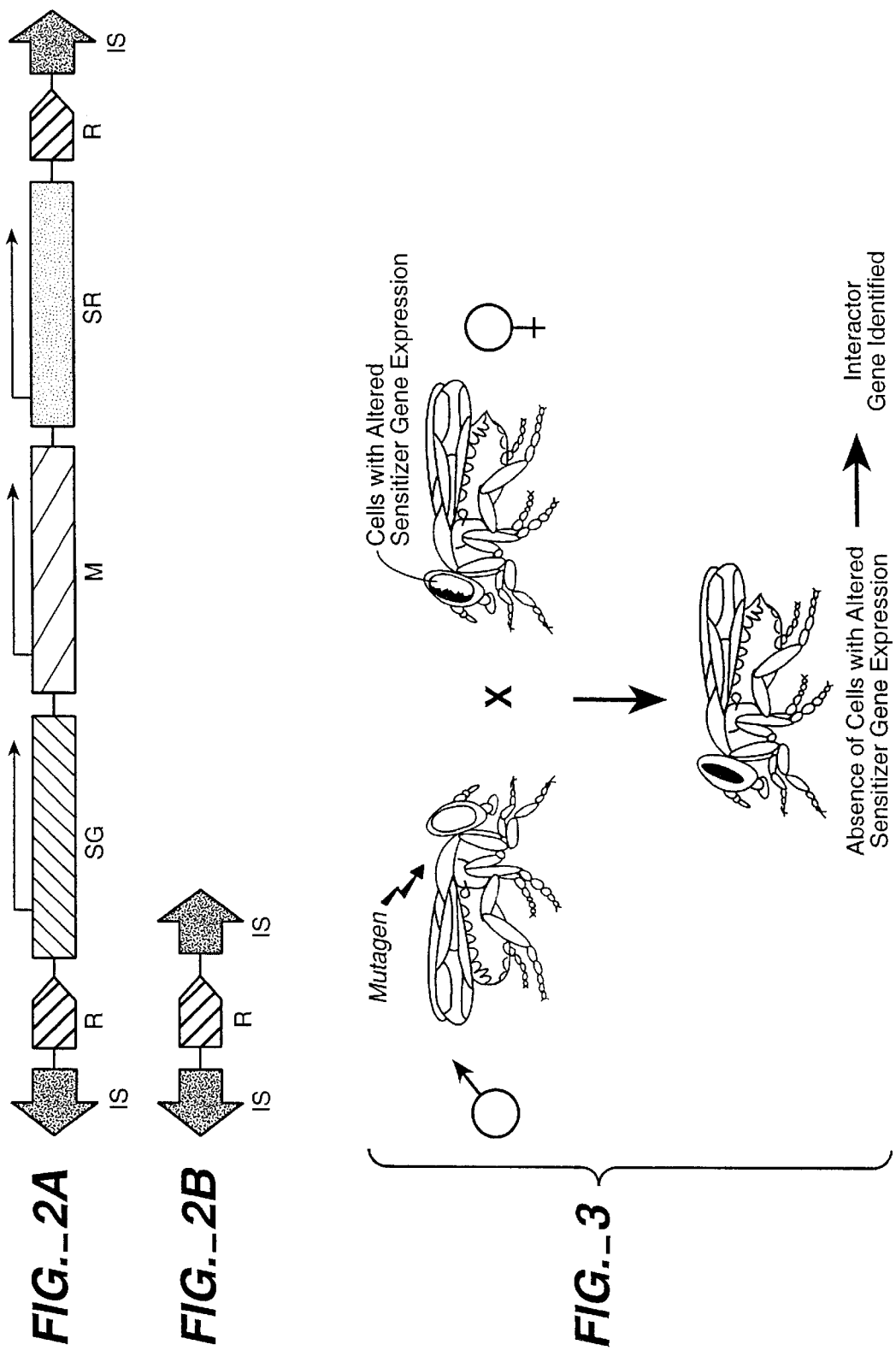
FIG._2A
FIG._2B
FIG._3

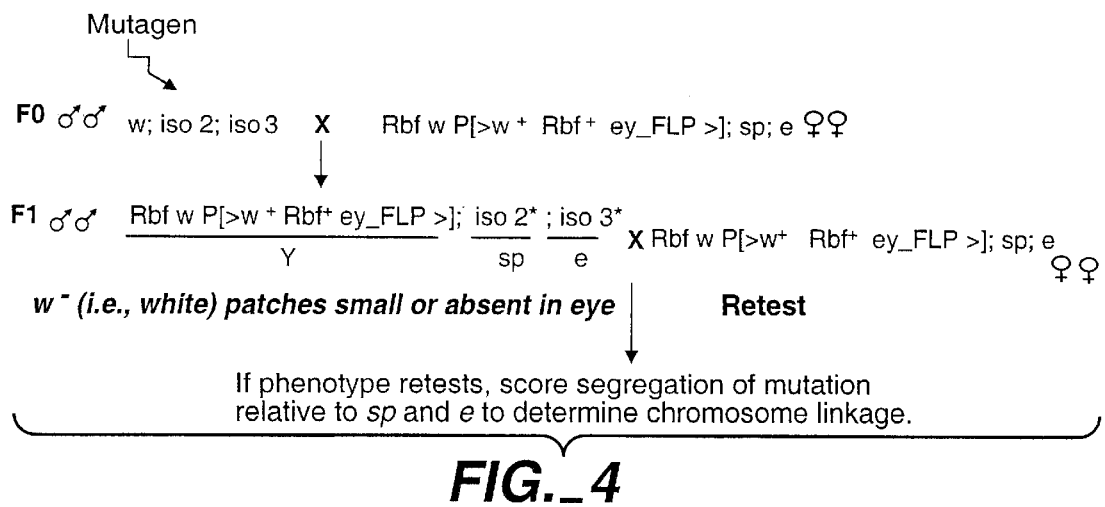
FIG._4
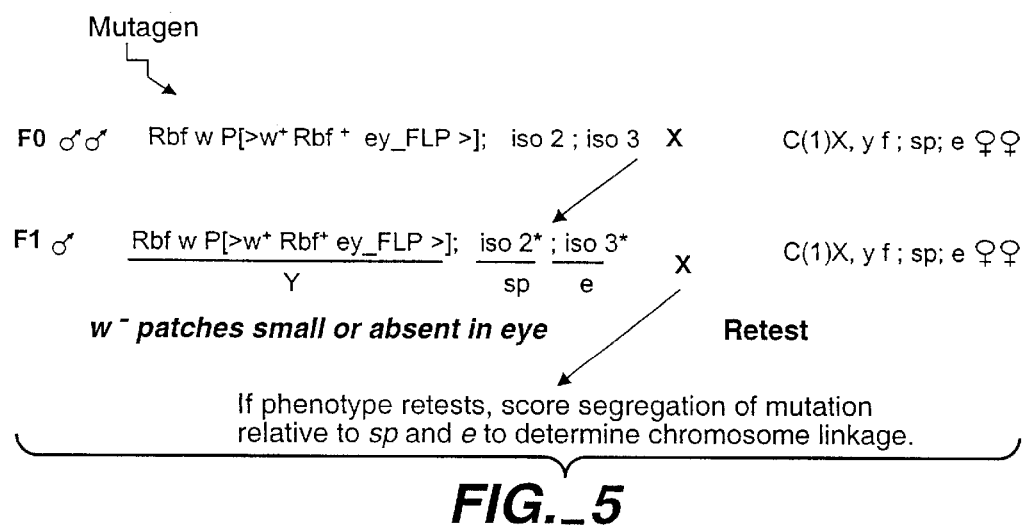
FIG._5
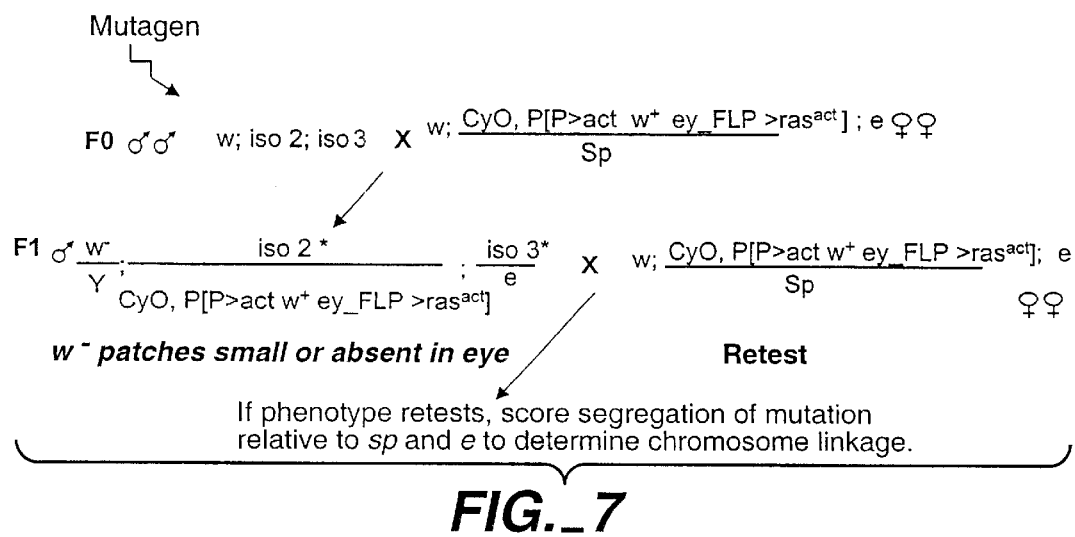
FIG._7

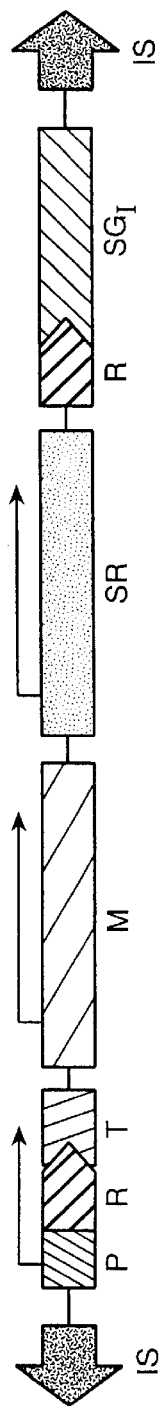
FIG._6A
FIG._6B
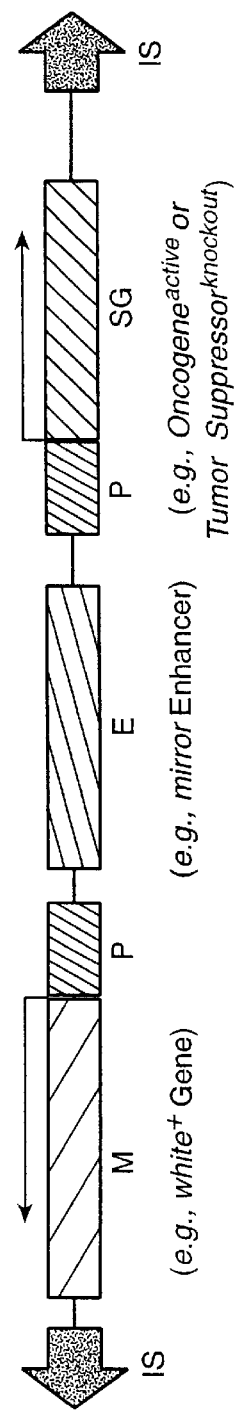
FIG._8

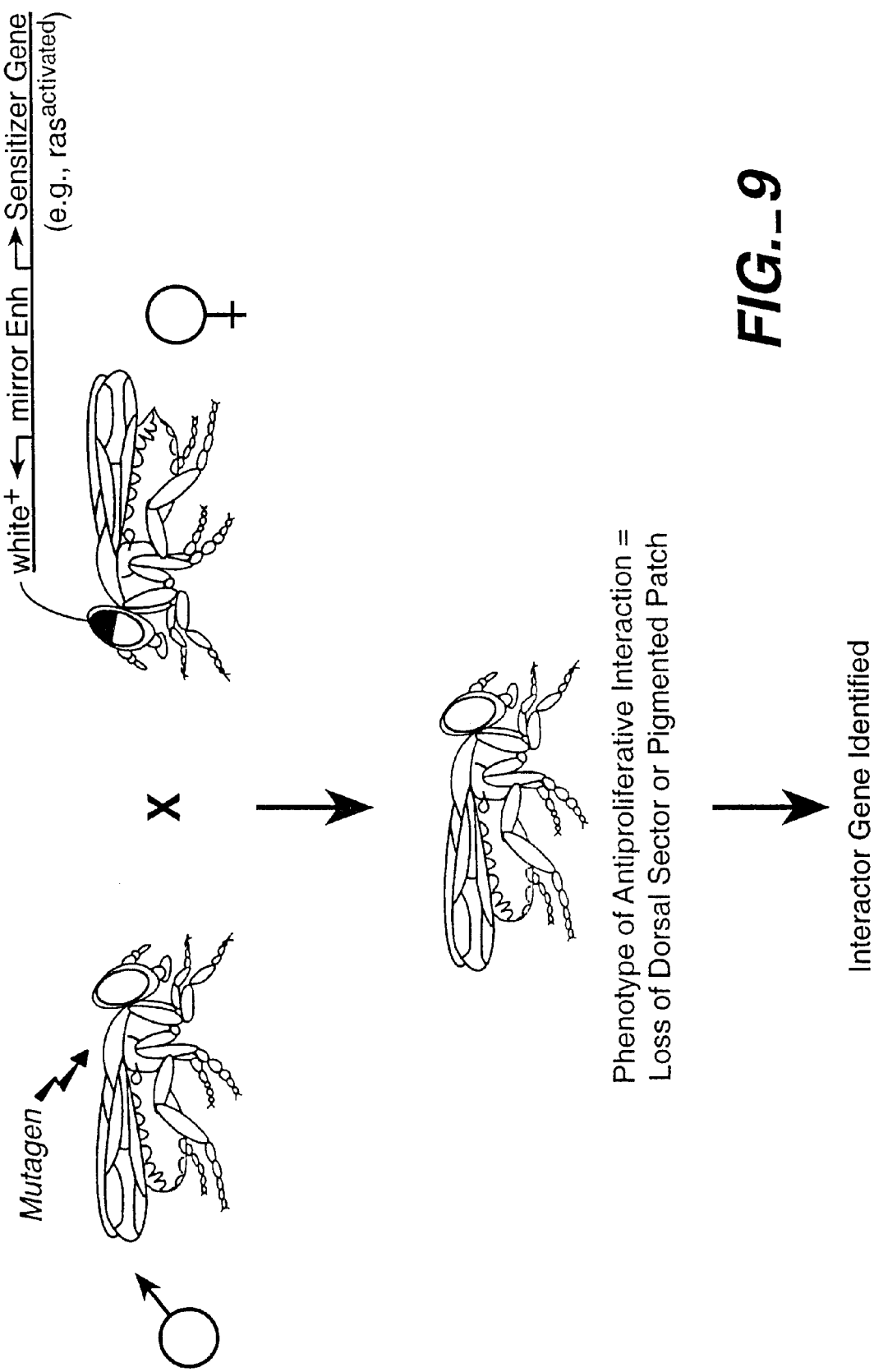
FIG._9

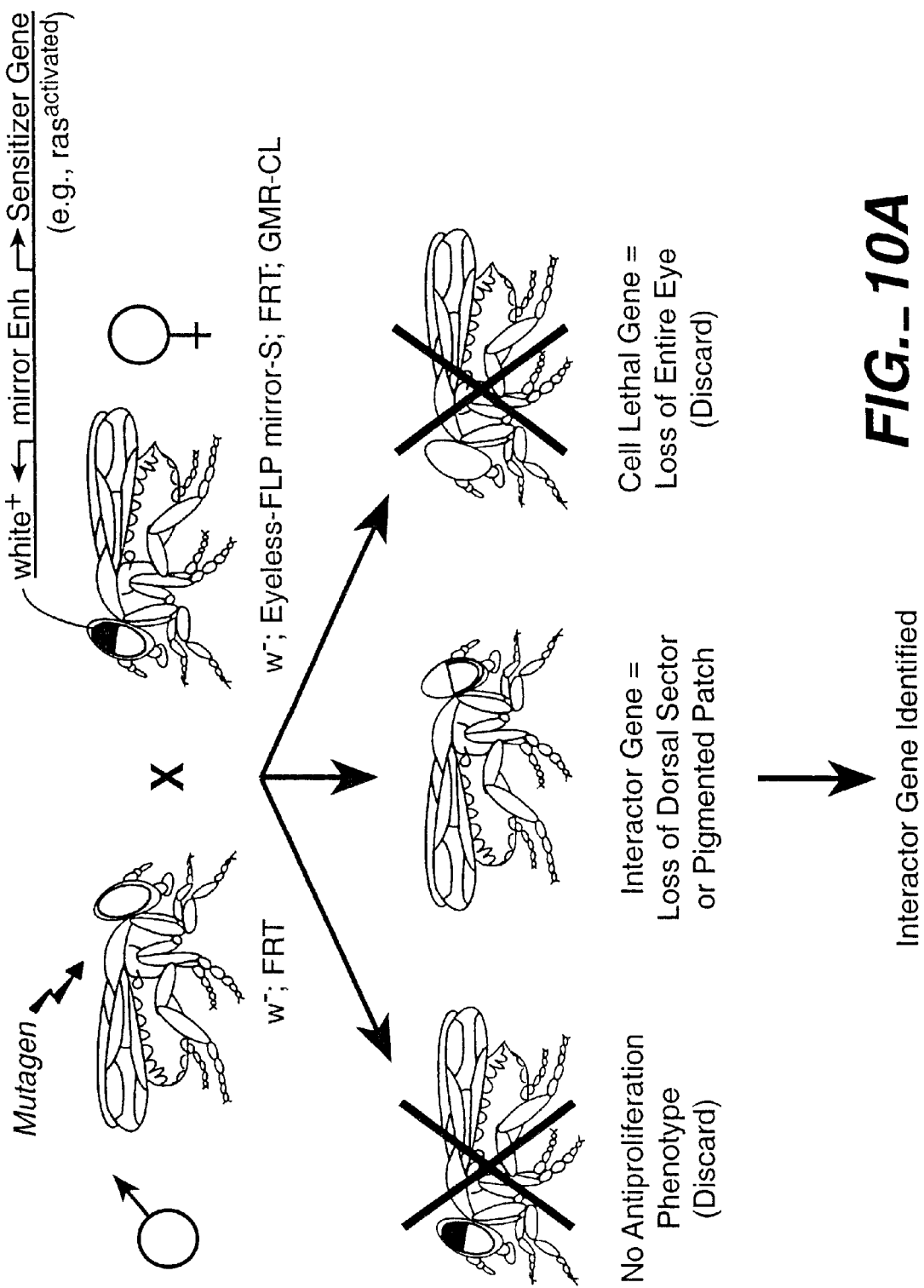
FIG._10A

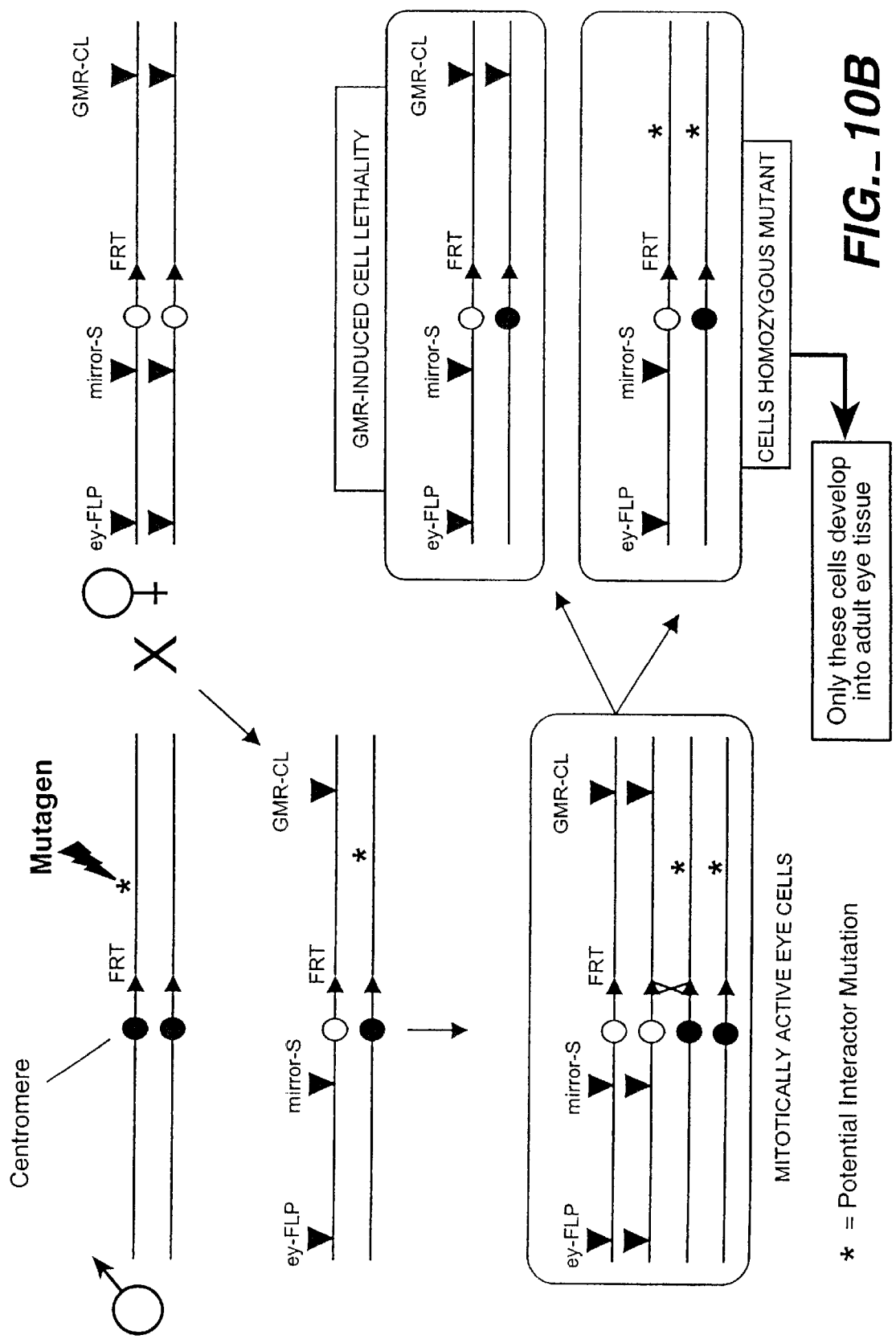
FIG._10B

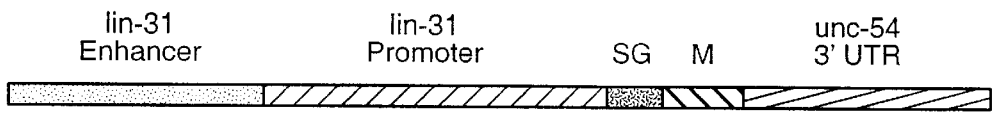
FIG._11
Ear Cartilage Specific Deletion of
p16Ink4 Tumor Suppressor Gene
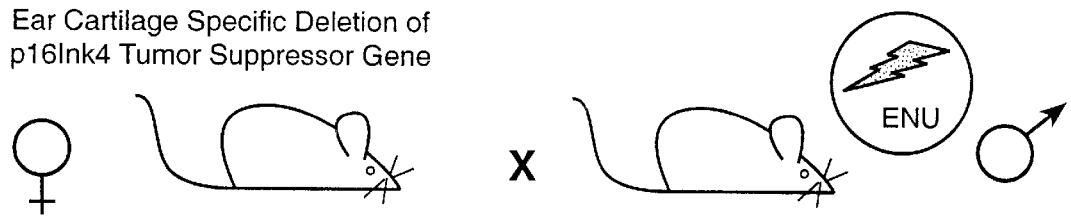
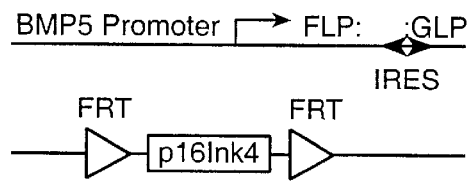
Phenotype of Antiproliferation Interaction =
Misshapen Ear Due to Death of Cartilage Cells

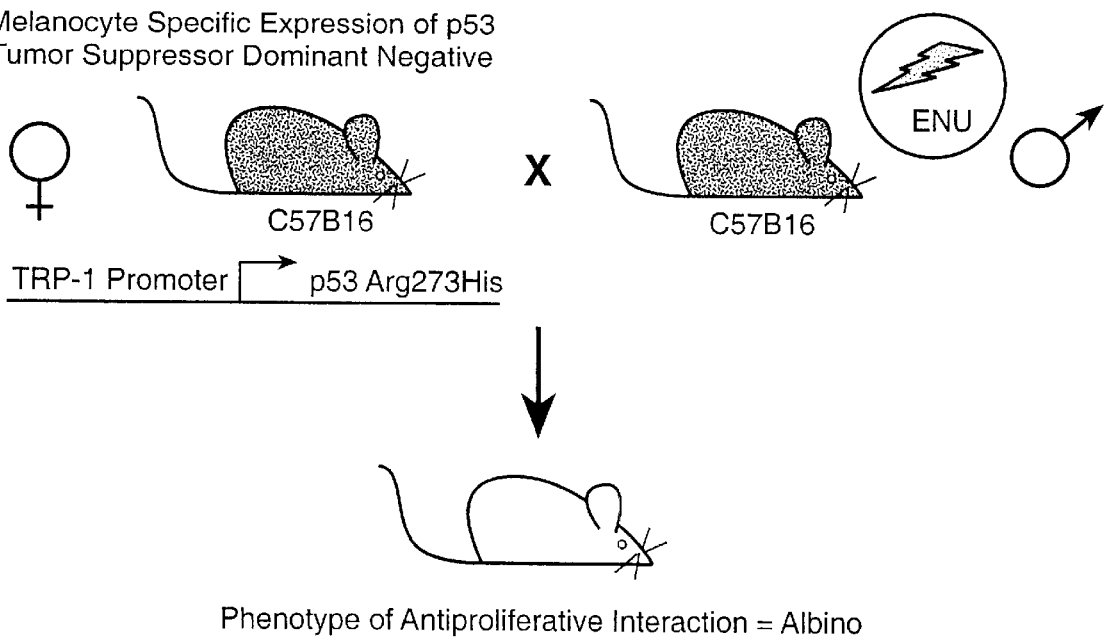
FIG._13
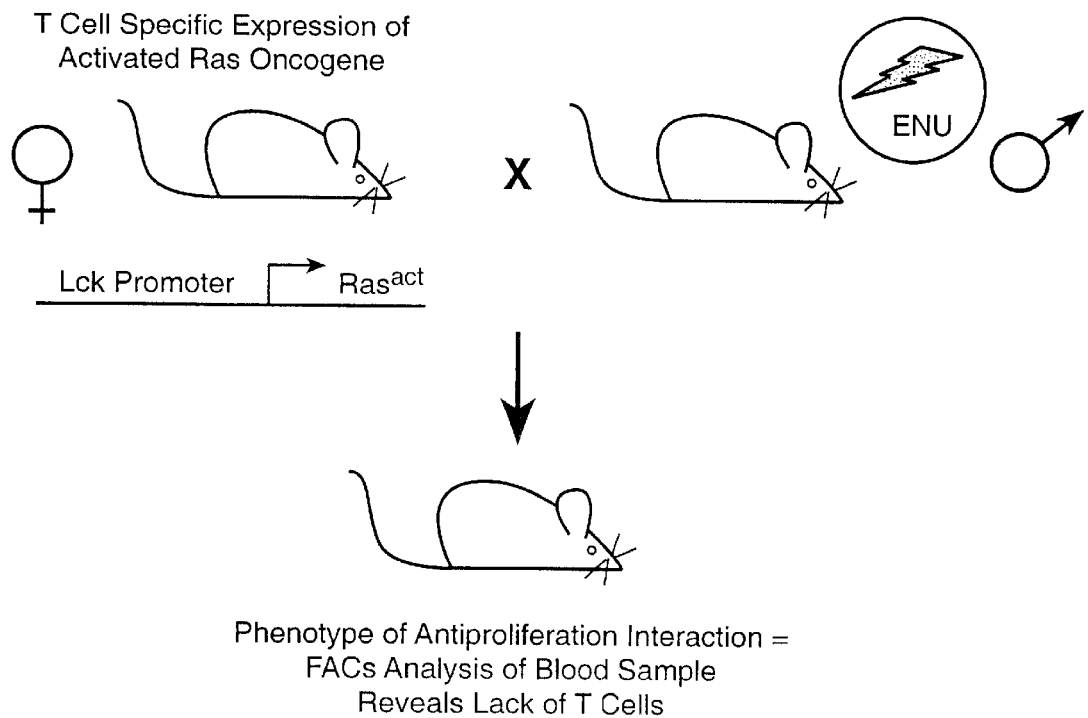
FIG._14

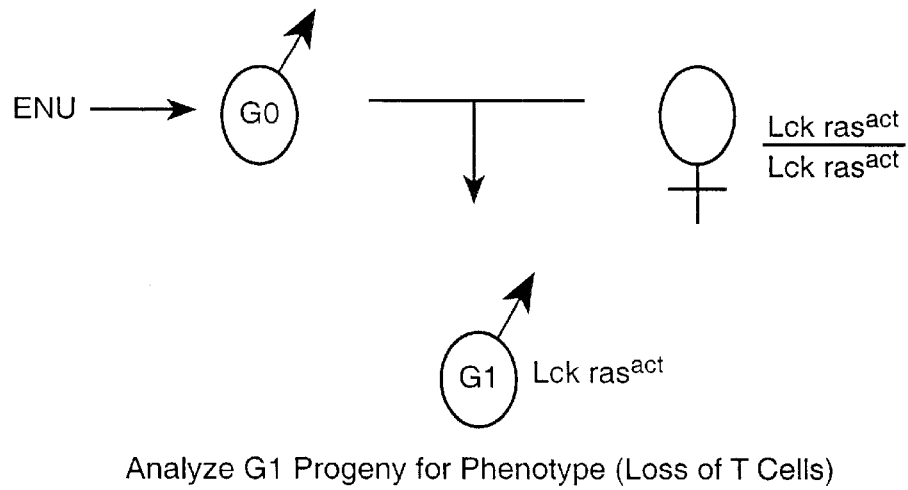
FIG._15A
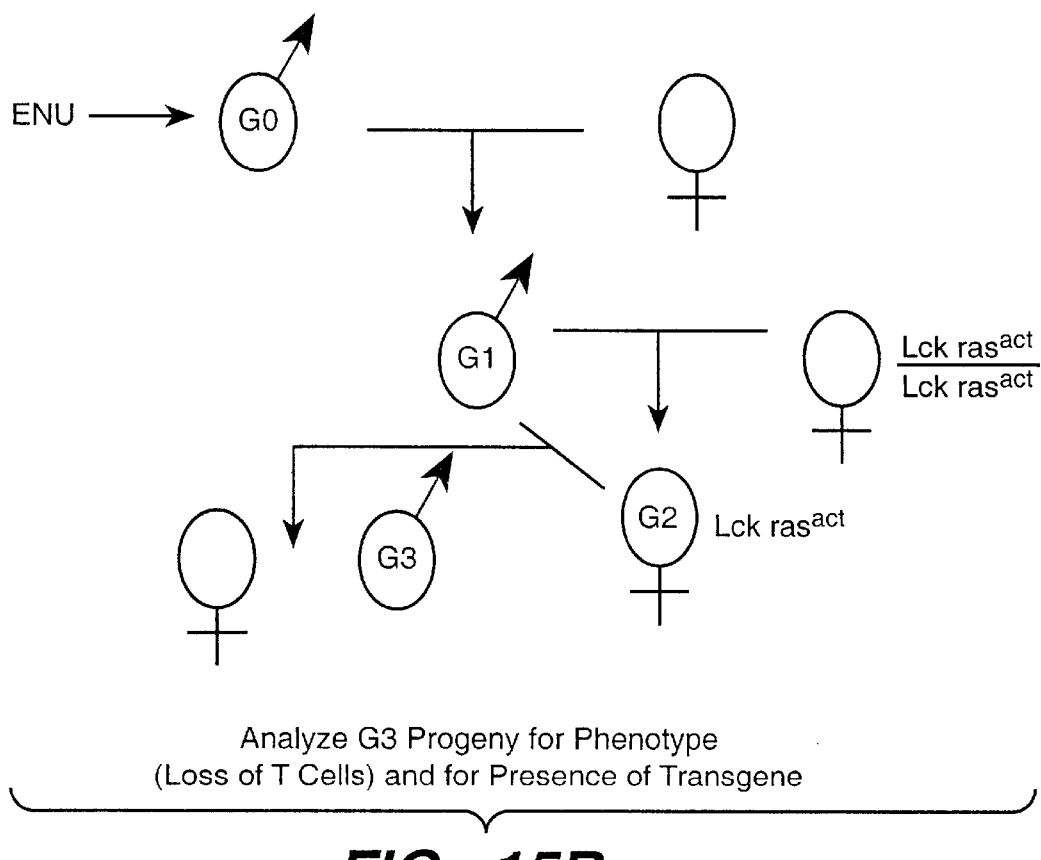
FIG._15B

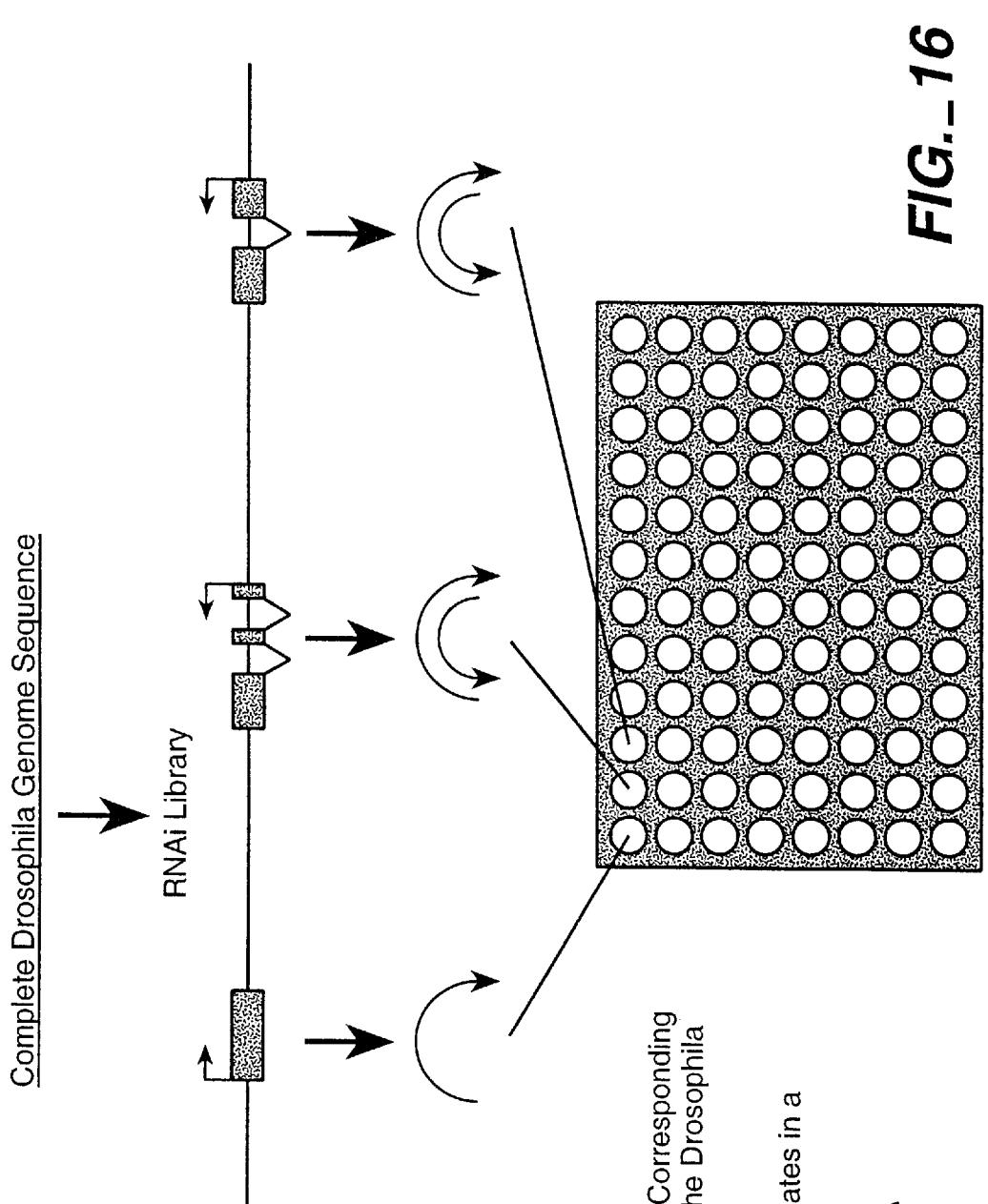
FIG._16

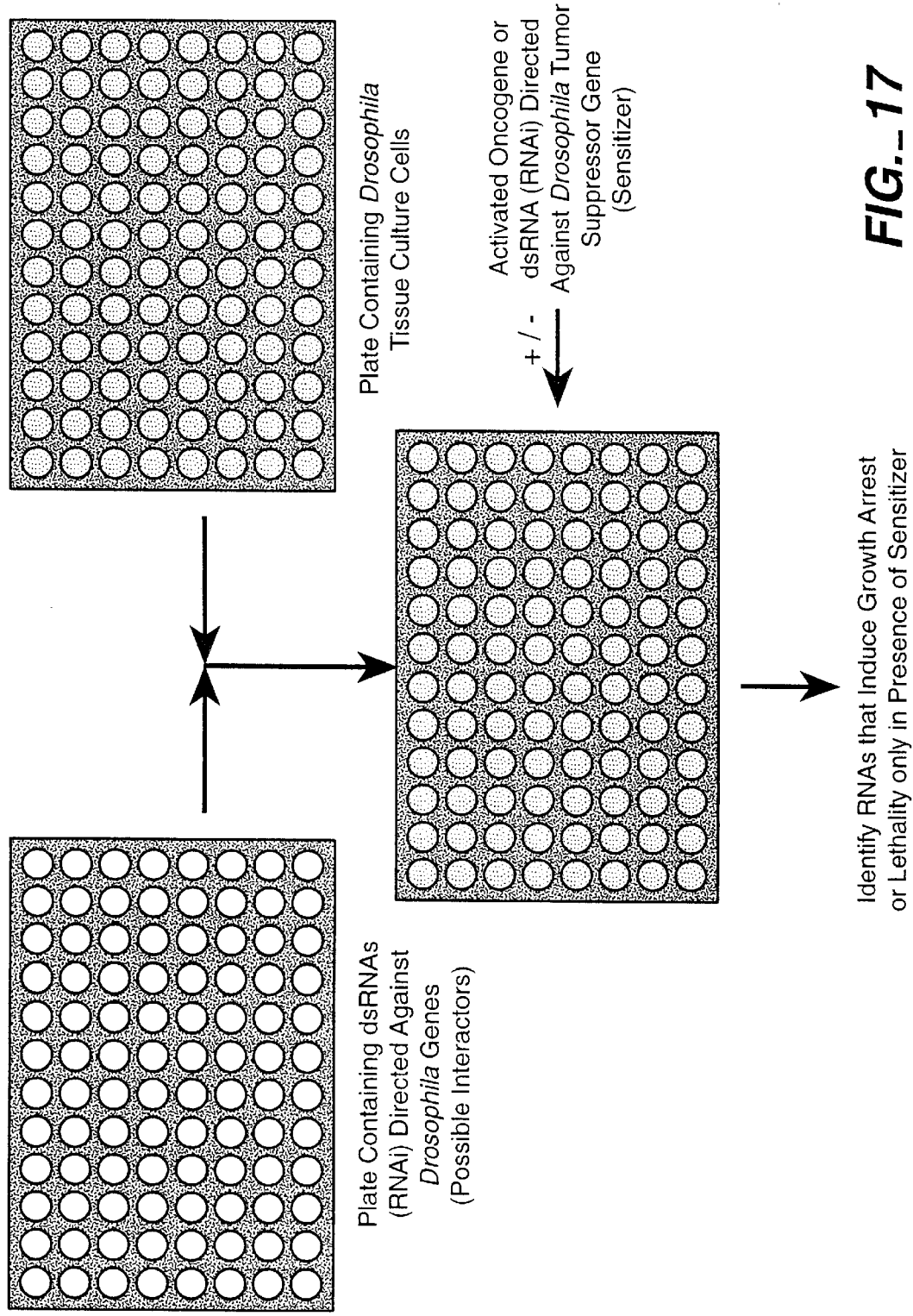
FIG._17

_US 6,531,644 B1_

METHODS FOR IDENTIFYING ANTI-CANCER DRUG TARGETS

REFERENCE TO RELATED APPLICATIONS

This application claims priority to U.S. application Ser. No. 60/176,372 filed Jan. 14, 2000, entitled "Methods for Identifying Anti-Cancer Drug Targets" which is incorporated by reference herein in its entirety.

FIELD OF THE INVENTION

The invention concerns genetic engineering and screening methods useful for the identification of gene targets for anti-cancer agents.

BACKGROUND OF THE INVENTION

Cancer is a complex and devastating group of diseases that kills one in five adults in developing countries. Although cancers arise from a wide variety of cells and tissues in the body, there are unifying features of this group of diseases. Cancer is predominantly a genetic disease, resulting from the accumulation of mutations that promote clonal selection of cells that exhibit uncontrolled growth and division. For example, by the time a tumor reaches a palpable size of about one centimeter, it has already undergone about thirty cell doublings, has a mass of approximately one gram, and contains about one billion malignant cells. The result of such uncontrolled growth of tumor cells is the formation of disorganized tissue that compromises the function of normal organs, ultimately threatening the life of the patient. Obviously, methods for prevention, early detection and effective treatment of cancer are of paramount importance.

The past twenty years of research on the mechanistic basis of carcinogenesis have resulted in a revolution in our understanding of the molecular nature of genetic changes that initiate tumor formation. Specific genes have been identified that are frequently mutated in tumor cells, many of which have been grouped into two main classes termed oncogenes and tumor suppressor genes. A few key genes have been identified that are very commonly mutated in a large number of different tumors, such as the oncogene ras and the tumor suppressor genes p53 and Rb. Furthermore, genes that are mutated in tumor cells tend to have functions that cluster in one of the following categories: DNA repair, chromosomal integrity, cell cycle control, growth factor signaling, apoptosis, differentiation, angiogenesis, immune response, and cell migration. Thus, it is clear that there are specific mutations in certain genes that distinguish cancer cells from normal cells.

Despite the fundamental significance of these discoveries, they have not been paralleled by the development of highly selective drugs to treat cancer. This lag in the development of practical therapeutic applications from these discoveries is due to several factors. An ideal chemotherapeutic must selectively kill or block the proliferation of tumor cells without having a deleterious effect on normal growing cells in the body. Most of the genetic alterations found in tumors cells that distinguish them from normal cells are either gain-of-function mutations in oncogenes, which result in increased expression or activity of the gene product, or loss-of-function mutations in tumor suppressor genes, which result in underexpression or lack of activity of the gene product. The protein products of oncogenes having gain-of-function mutations are technically difficult drug targets, due to the lack of effective strategies to selectively inhibit solely the excessive activity of the protein in tumor cells, without deleteriously affecting necessary levels of protein activity in normal cells. Conversely, tumor suppressor genes with loss-of-function mutations are also problematic as drug targets, as it is technically very difficult to develop small molecule drugs that restore the function of a missing or defective protein.

Thus, there is a need for systematic methods to identify highly selective drugs and their cognate targets for killing or inhibiting the proliferation of cancer cells by exploiting the specific genetic alterations that characterize tumor cells. Genetic screening in model organisms offers one possible solution to this challenge. Large-scale, systematic genetic screens in model organisms provide a technically feasible strategy for functionally analyzing nearly all genes and gene products within an organism that relate to a physiological process of interest, and are robust and efficient enough to identify extremely rare genetic mutations. This approach has been used routinely to dissect physiologically important pathways in a number of genetically facile species including the baker's yeast _Saccharomyces cerevisiae_, the nematode _Caenorhabditis elegans_, the fruit fly _Drosophila melanogaster_, the zebrafish _Danio rerio_, and the mouse _Mus musculus_. With respect to using these model organisms for analyzing processes that relate to human disease, each model organism has its own advantages and disadvantages which generally reflect a balance of technical ease of manipulation versus direct relevance to human genetics and physiology. Factors affecting technical ease of use in each system include generation time, cost of growth and maintenance, genome size, and availability of tools for genetic engineering, mutagenesis, gene mapping, and gene cloning. Consequently, the unicellular yeast _S. cerevisiae_ offers perhaps the greatest technical facility for genetic screens with a short generation time of only 2 hours, a haploid phase of the life cycle, and a small genome size less than $\frac{1}{100}$ that of human; however, this system suffers from the fact that baker's yeast is a unicellular organism and many genes and pathways involved in intracellular communication, differentiation, and growth control in humans are completely absent in _S. cerevisiae_. Conversely, as a mammal the mouse is clearly the most similar model organism in genome organization and physiology to human, but suffers from that fact that growth, maintenance, and manipulation of mice is relatively cumbersome, time consuming and expensive. Accordingly, the invertebrate animal model organisms, _C. elegans_ and Drosophila, have found favor for large scale genetic screens because they have provided an especially effective comprise between ease of manipulation and functional relevance to human physiology.

Beyond the issues of the technical feasibility of performing large scale genetic screens with model organisms, properly designed genetic screening strategies provide an efficient and logically rigorous method to identify ideal drug targets. Most drugs act by specifically inhibiting the activity of the target proteins with which they associate. And, most mutations generated by mutagenesis in genetic screens are loss-of-function mutations which reduce the expression or activity of the protein products of those genes. Thus, it follows that a loss-of-function mutation can be considered a surrogate for the effect of a drug that specifically inhibits the activity of the protein product of that gene; and further a loss-of-function mutation in a gene which produces a phenotype in vivo that mimics a desired therapeutic effect therefore identifies as a potential drug target the protein product of that mutant gene. So, the challenge in using genetic screens to identify novel drug targets for a particular disease is to carefully design the screen such that the desired loss-of-function mutations, which simulate the ideal therapeutic effect of a drug in vivo, can be readily and efficiently selected by virtue of a specific, easily scored phenotype.

In fact, large scale genetic screens in model organisms have been extensively employed to dissect genetic and biochemical pathways that relate to fundamental aspects of cancer biology. For example, genetic analysis of yeast has proven to be a very valuable approach to identify genes and proteins involved in DNA repair (Friedberg, Micrbiol Rev (1988) 52:70) and control of the cell cycle (Hartwell, J. Cell Biol. (1980) 85:811–822). Genetic analysis in the nematode C. elegans has led to important discoveries regarding growth factor signaling, for example through the ras pathway (Kayne and Sternberg, Curr Opin Genet Dev (1995) 5:38–43), and factors involved in controlling apoptosis (Ellis and Horvitz, Cell (1986) 44:817–829). Similarly, large scale genetic screens in the fruit fly Drosophila have also led to the discovery of novel components of cancer associated signal transduction pathways, including the ras (Karim et al., Genetics (1996) 143:315–329), notch (Go and Artavanis-Tsakonas, Genetics (1998) 150:211–220), dpp (Raftery et al., Genetics (1995) 139:241–254), and hedgehog (Hooper and Scott, Cell (1989) 59:751–765) pathways. Indeed, gene mutations in Drosophila that affect tumor formation in this simple invertebrate organism were identified as long as 80 years ago (Stark, J. Cancer Res. (1918) 3:279–299; Gateff and Schneiderman, Natl. Cancer Inst Monogr (1969) 31:365–397). The physiological relevance of Drosophila tumors to those of mammals has been convincingly demonstrated by studies of the *lats* tumor suppressor gene. Mutations in the *lats* gene in Drosophila were first discovered in genetic screens specifically designed to identify tumor suppressor-like genes in this organism (Xu et al., Development (1995) 117:1223–1237). In these studies, genetically mosaic Drosophila were generated containing clones of cells with homozygous mutations in the *lats* gene, and these clones of mutant cells were found to develop into large tumors. Most importantly, human and mouse homologs of the *Drosophila lats* gene were identified, and knockout mice genetically engineered to contain homozygous mutations in the *Lats* gene developed soft-tissue sarcomas, ovarian stromal cell tumors, hyperplastic changes in the pituitary, and were highly sensitive to carcinogenic treatments (St. John et al., Nat Genet (1999) 21:182–186) thereby validating the physiological relevance of tumor suppressor genes in Drosophila with counterparts in mammals. The technical obstacles posed by mammalian model systems such as the mouse have made it more costly and less practical to pursue large scale mutagenesis schemes by comparison with the simpler invertebrate organisms; nonetheless, recent progress has provided tools to perform in vivo mutagenesis in the mouse efficiently enough to enable phenotype-based genetic screens (McDonald, Proc Soc Exp Biol Med (1995) 209:303–308; Beddington, Curr Biol (1998) 8:R840–R842; Schimenti and Buchan, Genome (1998) Res 8:698–710). With respect to applications to cancer, a genetic screen in the mouse using the chemical mutagen ethylnitrosourea was used to identify a dominant mutation that predisposes to spontaneous intestinal cancer (Moser et al., Science (1990) 247:322–324). Subsequent characterization of this particular mutation revealed that the mutant mice contained a genetic lesion in the murine homolog of the human APC gene, a gene mutated in patients afflicted with familial adenomatous polyposis which predisposes to colorectal cancer, and which is also mutated in sporadic colorectal cancers (Su et al., Science (1992) 256:668–670). As a further variation beyond ordinary phenotype-based forward genetic screening in the mouse, methods for genetic modifier screens have been proposed based on the identification of mutations that enhance or suppress a starting index phenotype of interest, such as modification of the predisposition to intestinal cancer caused by mutations in the murine homolog of the APC gene (U.S. Pat. No. 5,780,236).

Although all of the genetic screening approaches in model organisms described above have proven their utility in the context of basic research, it is significant to note that the general object of such screens is to systematically identify as many components as possible of biological pathways of interest, for example those biological pathways linked to cancer. Importantly, such screens are not designed to selectively identify genes encoding proteins having properties expected for ideal anti-cancer drug targets. Thus, much time and effort must be invested to carry out functional analysis and validation on the genes arising from such screens to identify those few which are most promising as practical drug targets. More recently, a type of genetic screen directly aimed at identifying drug targets for the treatment of cancer has been described (PCT WO9924603; Hartwell et al., Science (1997) 278:1064–1068; Friend and Oliff, New Eng. J. Med. (1998) 338:125–126). This directed genetic screen has been most well-defined in its application in the yeast *S. cerevisiae*, and is actually based on a well-established method in yeast genetics termed a "synthetic lethal screen" which has been commonly employed as a tool to investigate redundant genetic functions in yeast (Botstein, Harvey Lectures (1987) 82:157–167; Doye and Hurt, Trends Genet (1995) 11:235–241). As a directed strategy to identify anti-cancer drug targets using yeast genetics, the standard synthetic lethal screening strategy has been modified slightly by starting with a yeast strain that contains a primary mutation in a yeast gene that is homologous to a human or mammalian gene mutated in cancer cells, for example a mutant yeast strain modified in the DNA repair genes MLH1 or MSH2 (CT WO9924603; Hartwell et al., supra). As a consequence, this variation of a synthetic lethal genetic screen specifically selects for secondary mutations which result in a lethal phenotype in yeast only in the context of a primary mutation within a yeast homolog of a human cancer-associated gene (such as MLH1 or MSH2), but not in the context of the wild-type form of the cancer-associated gene.

The underlying logic of using a synthetic lethal screen in yeast to identify anti-cancer drug targets is sound, but it poses serious limitations with respect to ultimate applicability to human cancer. In particular, homologs of many of the genes and pathways that are the most commonly mutated in human cancer are completely missing in yeast and are beyond the scope of these screens- including Rb, p53, growth factor signaling, and apoptosis pathways. It is these genes that clearly represent the most desirable starting points for such a screen as the resulting drug targets would have the broadest clinical applicability across different forms of cancer. The absence of these most common cancer associated genes and pathways in yeast reflects that fact that *S. cerevisiae* is a very simple unicellular organism. This leads to the question of whether the methods of the yeast synthetic lethal screen to identify anti-cancer drug targets can be directly transferred to a more complex multicellular metazoan animal, such as the nematode *C. elegans*, the fruit fly Drosophila or the mouse, where the common cancer-associated pathways are present. Unfortunately, this is not feasible as the yeast genetic screening method relies on plasmid manipulation techniques that are not applicable in metazoans. Also, the screening methods in yeast take advantage of the haploid life cycle in this organism, where there is just a single copy of each yeast gene, to efficiently identify genes where loss-of-function mutations would otherwise be recessive.

Although synthetic lethal genetic interactions have long been known in metazoan animal genetics (Dobzhansky, Genetics (1946) 31:261–290), a genetic screen based on identification of an organismal synthetic lethal phenotype would be extremely inefficient in metazoans, due to the inability to directly recover the secondary mutation from the dead animals for further analysis and characterization. As a result, other forms of genetic screens to selectively identify anti-cancer drug targets have been proposed for use in metazoans as substitutes for a true synthetic lethal screening strategy. Specifically, it has been suggested that a genetic modifier screen in Drosophila based on identifying mutations that act as enhancers of a rough eye phenotype induced by ectopic expression of dmyc (a homolog of the human myc oncogene) would be the "conceptual equivalent" of synthetic lethal mutations; hence, the genes having the enhancer mutations would have the properties of ideal anti-cancer drug targets (WO 99/24603). Actually, this is not the case; enhancer mutations arising from such a dmyc misexpression modifier screen would generally identify genes whose normal role is to down-regulate the activity of the dmyc pathway, and these enhancer mutations would not necessarily exhibit the desired property of a mutation in a gene encoding an ideal anti-cancer drug target, i.e. specifically killing or inhibiting the proliferation of only those cells were the dmyc oncogene is abnormally overexpressed.

In view of the foregoing, it is apparent that improved methods for identifying anti-cancer drug targets are highly desirable.

SUMMARY OF THE INVENTION

The invention provides highly selective methods for the identification of anti-cancer drug targets. One method comprises recombinantly modifying a non-human metazoan animal to mis-express a tumor gene or an oncogene (collectively referred to as "sensitizer genes") in a target tissue. Preferably the non-human animal is one that is commonly used in genetic studies (e.g. Drosophila, C. elegans, or mouse). The target tissue is dispensable for viability and reproduction of the animal. In some embodiments, mis-expression of the sensitizer gene results in abnormal proliferation of the target tissue, while non-targeted tissues of the recombinantly modified animal exhibit normal proliferation. Progeny of the recombinantly modified animal are generated that have mutations in putative "interactor" genes that may result in sensitizer gene-specific antiproliferation or killing of the target tissue. The interactor gene mutations may be specifically targeted, for example using RNA interference to knock out gene function, or may be randomly generated using chemical, radiation, or transposon mutagenesis. Progeny are identified that have a reduction in size or absence of the target tissue, but have normal non-target tissues. These animals, which are said to exhibit sensitizer gene-specific antiproliferation phenotypes, are further evaluated to determine whether they have mutatations in interactor genes that cause the phenotype. Interactor genes and homologues and orthologs thereof, are isolated and used to identify anti-tumor compounds.

In an alternative embodiment of the invention, the recombinantly modified animals and their progeny are used to directly screen anti-tumor compounds. Test compounds are administered to the animals in varying doses. Compounds that cause a reduction in size of the target tissue and have no adverse effects on non-target tissues are further evaluated as putative anti-tumor compounds.

The invention also provides various novel transformation constructs that can be used to generate novel transgenic animals that have altered expression of a sensitizer gene in a target tissue. The constructs are diagrammed in FIGS. 2, 6, and 8, and are described in detail in the specification.

In another alternative embodiment of the invention, RNA interference (RNAi) is used in cell culture-based screens to identify interactor genes that exhibit sensitizer gene-specific antiproliferation phenotypes, or as confirmation screens of interactor genes identified in the progeny of the recombinantly modified animals.

The entire contents of all references, including patent applications, cited herein are incorporated by reference in their entireties for all purposes. Additionally, the citation of a reference in the preceding background section is not an admission of prior art against the invention described herein.

BRIEF DESCRIPTION OF THE DRAWINGS

FIGS. 1A–1C: FIG. 1A depicts a cell having mutation X in a sensitizer gene (e.g. an oncogene or a tumor suppressor gene) which leads to abnormal cell proliferation. FIG. 1B depicts a cell also having mutation X, and additionally having mutation Δ in an interactor gene. The combination of mutations in the sensitizer gene and the interactor gene result in cell death. FIG. 1C depicts a viable, non-tumorigenic cell having the same mutation Δ as the cell of FIG. 1B, but lacking mutation X in the sensitizer gene.

FIGS. 2A & 2B: FIG. 2A shows a transformation construct that can be used to identify interactor gene mutations that result in antiproliferation of tumor cells with mutant tumor suppressor gene function. The construct comprises insertion sequences (IS), recombinase target sites (R), a sensitizer gene (SG) (e.g. a tumor suppressor gene), a marker gene (M) and a gene comprising sequences that encode a site-specific recombinase (SR) operably linked to a promoter that is active in a tissue non-essential for viability. FIG. 2B shows the appearance of the construct after recombination occurs between the recombinase target sites in tissues where there is expression of the site-specific recombinase.

FIG. 3 depicts a sensitizer gene-specific antiproliferation screen that employs female flies containing the construct depicted in FIG. 2A.

FIG. 4 shows a genetic strategy for identifying Rb sensitizer gene-specific antiproliferation mutations on chromosomes 2 and 3 in Drosophila using the construct depicted in FIG. 2A and the screening method depicted in FIG. 3.

FIG. 5 shows a genetic strategy for identifying Rb sentizer gene-specific antiproliferation mutations on chromosomes X, 2, and 3 in Drosophila using the construct depicted in FIG. 2A and the screening method depicted in FIG. 3.

FIGS. 6A & 6B: FIG. 6A shows a transformation construct that can be used to identify interactor gene mutations that result in antiproliferation of tumor cells with altered oncogene function. The construct is similar to that shown in FIG. 2A, but in addition has a promoter sequence (P) between the 5' insertion sequence and recombinase target site, and a transcription termination/polyadenylation sequence (T) at the 3' end of the 5' recombinase target site that prevents promoter activity. An inactive sensitizer gene (SG$_i$), i.e. an oncogene lacking promoter/enhancer elements, is downstream of the 3' recombinase target site. When recombinase is expressed, the sequences between the recombinase sites are excised thereby activitating the sensitizer gene (SG$_A$), as depicted in FIG. 6B.

FIG. 7 shows a genetic strategy for identifying interactor gene mutations that cause sensitizer gene-specific antiproliferation in the progeny of Drosophila that have been recombinantly modified using the transformation construct of FIG. 6A to express a constitutively activated oncogene.

FIG. 8 shows a transformation construct that can be used to identify dominant or recessive mutations in interactor genes that specifically kill cells with a constitutively activated oncogene, a dominant negative form of a tumor suppressor gene, or a tumor suppressor gene that has been inactivated by an RNA interference molecule (RNAi) directed against it. Two promoters (P), facing opposite orientations, flank a tissue-specific enhancer element (E) which drives tissue-specific expression from both promoters, one promoter driving expression of a marker gene (M), and the other driving expression of the sensitizer gene (SG).

FIG. 9 depicts a screen employing the construct of FIG. 8 for the identification of dominant mutations in interactor genes that cause sensitizer gene-specific antiproliferation.

FIGS. 10A & 10B: FIG. 10A depicts a screen employing the construct of FIG. 8 for the identification of recessive mutations in interactor genes that cause sensitizer gene-specific antiproliferation. FIG. 10B shows the genetic strategy.

FIG. 11 depicts a transformation construct that can be used for vulval-specific expression of an altered sensitizer gene (SG) in C. elegans. The lin-31 enhancer/promoter directs expression in vulval precursor cells. Successful transformation is detected by abnormal vulva morphology and, optionally, expression of a marker gene (M). The 3' UTR of the unc-54 gene is provides polyadenylation and message stability.

FIG. 12 depicts a screen for the identification of interactor genes causing sensitizer gene-specific antiproliferation in the ear cartilage of mouse with altered expression of a tumor suppressor gene.

FIG. 13 depicts a screen for the identification of interactor genes causing sensitizer gene-specific antiproliferation in mouse melanocytes with altered expression of a tumor suppressor gene.

FIG. 14 depicts a screen for the identification of interactor genes causing sensitizer gene-specific antiproliferation in mouse T-cells with altered expression of an oncogene.

FIGS. 15A & 15B show a one- and a three-generation recessive screen, respectively, in the mouse.

FIG. 16 shows the approach for generating a library of dsRNAs for RNAi directed against all or part of the genes encoded in the Drosophila genome and arrayed onto 96-well plates.

FIG. 17 shows the screening strategy using RNAi-mediated inactivation in Drosophila tissue culture cells for identifying interactor genes that cause sensitizer gene-specific antiproliferation.

DETAILED DESCRIPTION OF THE INVENTION

Improved methods for the systematic and highly selective identification of anti-cancer drug targets are described. The method employs genetic screens using non-human metazoan recombinant model organisms. This is advantageous over prior methods that utilize unicellular organisms, as metazoan organisms possess the genes and pathways most commonly mutated in human cancer. Thus the methods described herein are for the identification of anti-cancer targets with the broadest possible clinical applicability for treatment of different human tumors. Further, the genetic screening methods of the invention are significantly more selective than previously described methods where metazoan animals are used. This is because, in contrast to prior methods, the genetic screens of the invention are designed to identify gene mutations that exhibit antiproliferative or killing effects solely in cells of the target tissue that have altered sensitizer gene expression characteristic of cancer cells, and not in cells having normal sensitizer gene function. The methods of the invention can be applied to a wide range of metazoan species, including metazoan species useful for very large-scale systematic genetic screens, such as Drosophila and C. elegans, as well as species that are genetically and physiologically closely related to human, such as the mouse. Another advantage of the present method is that the recombinant metazoan animals that are used in the screens can also be used to directly screen or test the activity of potential anti-cancer compounds; or they can be used as animal models for testing other therapeutic strategies.

Non-human metazoan animals are recombinantly modified to have altered expression of a gene of interest that is targeted to tissues, or portions thereof, dispensable for the viability and reproduction of the animal. In one embodiment, altered expression results in abnormal proliferation of cells of the targeted tissue(s). Preferably, the altered expression is heritable. The gene of interest is referred to herein as a "sensitizer gene". Typically, the sensitizer gene is selected because it is a homolog or ortholog of a known tumor suppressor gene or oncogene. The altered expression of the sensitizer gene may result from any suitable recombinant method such as knocking-out an endogenous tumor suppressor gene in the target tissue, inserting a dominant-negative tumor suppressor gene that interferes with endogenous tumor suppressor function, introducing constitutively active oncogenes, etc. In other embodiments, the animal may be engineered to express nucleic acid or protein that intereferes with endogenous sensitizer gene function, for example, by antisense DNA, RNA interference, peptide and RNA aptamers, etc.

The recombinant animals are used in genetic screens in which genes are identified that, when mutated, specifically kill or reduce the size of the target tissue. The identified genes exhibiting this specific killing or antiproliferative effect are referred to herein as "interactor genes." The killing/antiproliferative interaction is "specific" because it is limited to tissues that have altered expression of the sensitizer gene and does not occur in normal tissues (i.e. tissues that do not contain the altered sensitizer gene). The phrase "sensitizer gene-specific 'antiproliferative' or 'antiproliferation' phenotype" will be used herein to describe the killing or reduction in size of the tissue(s) in which expression of the sensitizer gene has been modified. The most preferred antiproliferative phenotype is a cell-lethal phenotype, i.e., elimination of some or, more preferably, all of the tissue(s) that have altered sensitizer gene expression. But phenotypes resulting in an inhibition of tumor growth are also useful. Interactor genes identified as having a sensitizer gene-specific antiproliferative phenotype are identified as putative anti cell proliferation drug targets for the treatment or management of cancer, tumor formation, and other conditions involving abnormal proliferation, or cell-cycle diseases and disorders.

Generation of Recombinant Animals with Altered Expression of Sensitizer Genes

As used herein, the term "recombinant animal" or "recombinantly modified animal" refers to any animal containing one or more cells bearing genetic information altered or received, directly or indirectly, by deliberate genetic manipulation at a subcellular level, such as by targeted recombination or microinjection or infection with recombinant virus, and encompasses animals in which one or more cells are altered by, or receive, a recombinant DNA molecule. The recombinant DNA molecule may be specifically targeted to a defined genetic locus, may be randomly integrated within a chromosome, or it may be extrachromosomally replicating DNA.

Preferably, the metazoan animal is a model organism that is routinely used in genetic studies, as tools will be readily available for genetic manipulation of the animal. The invention is exemplified with a detailed discussion of the use of Drosophila melangogaster (hereinafter Drosophila), Caenorhabditis elegans (hereinafter C. elegans), and the mouse. However, other model organisms can also be used in the practice of the invention (e.g. Xenopus, rat, chicken, zebrafish, etc.).

The sensitizer gene is one that can be mutated, or have a product with altered expression in cells of an identifiable tissue, or portion thereof, that is dispensable for viability and reproduction of the animal. The terms "altered expression", "modified expression", or "mis-expression", as used herein interchangeably to encompass altered expression, modified expression, or mis-expression due to gene mutations. Thus, a misexpressed protein may be one having an amino acid sequence that differs from wild-type (e.g. by amino acid substitution or deletion). These terms also include ectopic expression (e.g. by altering the normal spatial or temporal expression), over-expression (e.g. by multiple gene copies), underexpression, and non-expression (e.g. by gene knockout or blocking expression that would otherwise normally occur, for example, by using antisense or RNAi). In some embodiments, the altered sensitizer gene expression results in abnormal proliferation of the target tissue.

It is estimated that approximately 90% of tumors harbor defects in genes that regulate cell-cycle progression. Thus, in one embodiment of the invention, the sensitizer gene is a cell-cycle progression gene such as p53, Rb, p27, p15, p16, Bub-1, LATS, CyclinE, E2F, genes encoding cyclin-dependent kinases, etc. Preferably, the sensitizer gene has been identified previously as an oncogene or tumor suppressor gene of the metazoan animal used in the screen, or is a homolog or ortholog of a human oncogene or tumor suppressor gene. Examples of human oncogenes of which homologs have been identified in one ore more model organisms include Ab1-1, Bc12, Ras, CDC25A, and CyclinB. Examples of human tumor suppressor genes of which homologs have been identified in one or more model organisms include BRCA1, Rb, p16, p53, VHL, and Beta-Catenin. A comprehensive list of oncogenes and tumor suppressor genes may be found at the website for the Cancer Genome Anatomy Project (CGAP) of the National Cancer Institute: http://www.ncbi.nlm.nih.gov//ncicgap/cgaptso.cgi. In Drosophila, preferred sensitizer genes include Rb, (Du and Dyson EMBO J. (1999) 18:916–925), ras (Fortini et al., Nature (1992) 355:559–561), lats (U.S. Pat. No. 5,994,503) and p53 (U.S. patent application Ser. No. 09/268,969, filed Mar. 16, 1999). In C. elegans, preferred sensitizer genes include ras (Eisenmann and Kim, Genetics (1997) 146:553–565), cdc25 (Ashcroft et al., Developmental Biology (1999) 206:15–32), cyclin E (Park et al, Development (1999) 126:4849–4860), cullin (Kipreos et al., Cell (1996) 85:829–839), Rb (Lu and Horvitz, Cell (1998) 95:981–991), cdk (Boxem et al., Development (1999) 126:2227–2239); and p21 (Hong et al., Development (1998) 125:3585–3597). In mice, preferred sensitizer genes include p16 (Serrano et al., Nature (1993) 366:704–707), p19 (Chan et al., Mol Cell Biol. (1995) 15:2682–2688) p53 (Zakout-Houri et al., Nature (1983) 306:594–597), lats (U.S. Pat. No. 5,994,503) and ras (Trahey and McCormick, Science (1987) 238:542–545).

A unique feature of the screening method is that the altered expression of a sensitizer is targeted to one or more specific and identifiable tissues, or portions thereof, dispensable for the survival and reproduction of the animal. Such tissue is referred to herein as "target tissue". Examples of preferred target tissues include the eyes and wings in Drosophila; the vulva, certain muscle and nervous system cells in C. elegans; and ears and certain skin and blood cells in the mouse. In one preferred embodiment, altered expression of the sensitizer gene occurs in only a portion, patch, sector or domain of the target tissue(s). This can make it easier to identify mutated interactor genes that consistently reduce or eliminate specifically that portion of the tissue in which the altered expression of the sensitizer gene is manifested. Also, with some tissues, such as the skin or blood, the whole tissue is not dispensable. Thus, altered sensitizer gene expression is targeted to only a portion or sector of the tissue, for example, in melanocytes of skin or T cells of blood, to maintain viability of the animal. The target tissue is one that is identifiable, in that changes in levels of cell proliferation of the tissue can be detected, either visually (e.g. changes in the size of a solid tumor, or the color of skin pigment) or by aided analysis (e.g. analysis of blood cells using a Fluorescent Activated Cell Sorter).

Expression of the sensitizer gene in only a portion of the animal's tissues may be accomplished by inserting a transgene using one of a variety of genetic methods for mosaic, conditional, and/or tissue specific expression. For example, site-specific recombinases (designated "SR" in FIGS. 2 and 6) can be used to control gene expression through site-specific recombination at recombinase target sites (designated "R" in FIGS. 2 and 6). Examples of recombinase:target sites include Flp:Frt (Golic and Lindquist, Cell (1989) 59(3):499–509), Cre:LoxP (Sauer and Henderson, Nucleic Acids Res. (1989) 17:147–61), Kw:Kw RS (Ringrose et al. (1997) Eur J Biochem 248:903–912), R:RS (Onouchi et al., Nucleic Acids Res (1991) 19:6373–6378), and phiC31 recombinase:attP/attB (Thorpe and Smith, Proc Natl Acad Sci USA(1998) 95:5505–10). Another method for driving transgene expression employs the Gal4/UAS system (Brand and Perrimon, Development (1993) 118:401–415). Typically, expression will be under control of tissue- and/or developmentally-specific regulatory elements (e.g. enhancers and/or promoters). Examples of regulatory elements in Drosophila include those derived from eyeless-(Hauck et al., PNAS (1999) 96:564–569), sevenless-(Bowtell et al., PNAS (1991) 88(15):6853–6857), mirror-(McNeill et al., Genes Devl. (1997) 11:1073–1082), and glass-responsive promoters/enhancers (Quiring et al., Science (1994) 265:785–789) which are useful for expression in the eye; and enhancers/promoters derived from the dpp or vestigal genes which are useful for expression in the wing (Staehling-Hampton et al., Cell Growth Differ. (1994) 5(6):585–593; Kim et al., Nature (1996) 382:133–138). In C. elegans, the lin-31 promoter is a preferred tissue-specific promoter for expression in the vulva (Miller et al., Genes Devel., (1993) 7:933–947). Other tissue specific promoters in C. elegans include the hlh-1 promoter for body muscle-specific expression, and the myo-2 gene promoter for pharyngeal muscle-specific expression. In the mouse, preferred tissue-specific promoters/enhancers include melanocytespecific tyrosine-related protein 1 (TRP-1) promoter, which drives expression in the skin (Hart, Semin Oncol (1996) 23(1):154–158; Carreira et al., Mol. Cell Biol (1998) 18(9) :5099–5108), the BMP5 promoter (DiLeone et al., Genetics (1998) 148(1):401–408) which drives expression in ear cartilage, and the Lck promoter which drives expression in T-cells (Wildin et al., J Immunol (1995) 155(3):1286–1295). Other promoters/enhancers are well-known in the art for limiting expression of a transgene in a cell- or tissue-specific manner in a model organism, and can be used.

In a preferred embodiment, detection of the misexpression of the sensitizer gene and/or the antiproliferative effects of interactor genes is facilitated by the presence or absence of marker gene expression in the target tissue. Ways in which marker gene expression or lack of expression can be accomplished is discussed in more detail below in connection with the transformation constructs of FIG. 2, FIG. 6, and FIG. 8. Any gene can be used as a marker that causes a reliable and easily scored phenotypic change in transgenic animals. In Drosophila, preferred marker genes include white and rosy which affect eye color. Other suitable marker genes in Drosophila include and yellow, ebony, singed, and Mwh, which are body color or morphology markers that may be used under tissue specific promoters. A comprehensive list of markers for Drosophila may be found in Ashburner (In *D. melanogaster*: A Laboratory Manual, (1989) Cold Spring Harbor, N.Y., Cold Spring Harbor Laboratory Press: pp. 299–418). A preferred marker in *C. elegans* is ncl-1 (Hedgcock and Herman, Genetics (1995) 141:989–1006), which causes enlarged nucleoli and is cell-autonomous, and thus, may be used under the control of any tissue-specific promoter. Green fluorescent protein (GFP) and LacZ are fluorescent and chromogenic reporters, respectively, that can serve as useful tissue specific markers in a variety of organisms, including Drosophila (Brand, Methods Cell Biol. (1999) 58:165–181), *C. elegans* (Chien et al., PNAS (1991) 88:9572–9582), and the mouse (Okabe et al., FEBS Let. (1997) 407:313–319; Zhou et al., Dev. Biol. (1997) 187:36–42; Godwin et al., Proc Nat. Acad Sci USA (1998) 95(22):13042–13047). Specific examples of how marker can be used are discussed below with regard to preparation of transformation constructs and in the Examples. For simplicity, reference to a "gene" in connection with the transformation constructs described herein, is intended to refer to any DNA (e.g. cDNA or genomic sequence) that encodes a gene product and may comprises any endogenous or heterologous non-coding regions, such as regulatory elements, unless otherwise indicated. The term "gene product" encompasses both encoded proteins and RNA (e.g. interfering dsRNA sequences).

Construct Design for Reduced Sensitizer Gene Expression or Activity

The design of transgene constructs used to cause altered expression of a sensitizer gene in a target tissue depends in part upon whether the goal is to mimic a loss of gene function (e.g. of a tumor suppressor gene) or a gain of gene function (e.g. an activated oncogene) in a tumor. To mimic the loss of function of a tumor suppressor gene, an animal's endogenous gene can be knocked out, and replaced using a rescue construct that allows function of tumor suppressor gene in all tissues except in the target tissue where the tumor suppressor gene is specifically disrupted. One way in which this can be accomplished is by using the transformation construct presented in FIG. 2A which contains three functional genes: 1) a functional copy of the sensitizer gene (SG); 2) a marker gene (M) that allows detection of transformation; and 3) sequence encoding a site specific recombinase (SR) under the control of an enhancer/promoter that restricts expression of the recombinase to a selected tissue or portion thereof dispensable for viability. These three genes, which can be arranged in any order, are flanked by direct repeats of the recombinase target site (R), which in turn are flanked by insertion sequences (IS) that incorporate the construct in the animals' genome. The insertion sequences can be derived from transposable elements that are commonly used to insert genes into model organisms, such as P-element, piggybac. Additional examples of suitable transposable elements from which the insertion sequences can be derived are listed under the subheading "Transposon Mutagenesis". This type of construct allows expression of the sensitizer transgene in any tissue except for the tissue in which the recombinase is expressed. In the target tissue where the enhancer/promoter that drives recombinase expression is active, recombination between the recombinase target sites causes excision of the sensitizer transgene from the chromosome (FIG. 2B). The excised transgene forms a free episomal circle. If the target tissue is mitotically active, the excised transgene will be lost upon further cell division.

In the fly, enhancers/promoters from eyeless or mirror can be used to target mitotically active eye discs; and enhancers/promoters from vestigal can be used to target mitotically active wing discs. Thus, when a construct is placed in an organism having a genetic background that is homozygous mutant for the endogenous sensitizer gene, such that there is a loss of gene function, the construct will rescue the function of the sensitizer gene in all tissues except the target tissue in which recombinase is expressed and the transgene excised. A genetic strategy using this type of construct in Drosophila is diagrammed in FIG. 4 and discussed in more detail in Example 1.

Another way of interfering with the activity of a sensitizer gene to cause a loss of gene function in a target tissue is to introduce a construct that causes expression of a dominant negative mutant of the sensitizer gene. Overexpression of the dominant negative protein blocks the function of the endogenous protein and thus mimics the effect of a loss of function mutation. This can be accomplished using a transformation construct such as that shown in FIG. 6. Similar to the construct described above, a tissue-specific enhancer is used to drive expression of a site-specific recombinase (SR) in a target tissue. In this case, however, the construct is designed so that recombination between the recombinase target sites causes the otherwise inactive sensitizer gene ($SG_I$ shown in FIG. 6A), to be expressed ($SG_A$ shown in FIG. 6B). Additionally, the marker gene (M) will be deleted in the target tissue.

In an alternative embodiment, a tissue specific enhancer can be used to directly drive overexpression of a dominant negative form of the sensitizer gene or another gene that dominantly interferes with sensitizer gene function (e.g. antisense, RNAi, etc., discussed further below). An advantage to this approach is that the loss of function phenotype is dominant, which eliminates the need to work in a homozygous mutant background. In addition, tissue-specific enhancers that drive sensitizer gene expression in non-dividing cells can be used since generating the "mutant" patch of cells does not require loss of the excised episomal DNA via mitosis. An example of such construct is depicted in FIG. 8. Another construct, that can be used for *C. elegans*, is illustrated in FIG. 11. In another alternative embodiment, antisense RNA or RNA interference (RNAi) is used to block the function of the endogenous gene/protein and thus mimic the effect of a loss of function mutation. Methods for using antisense RNA and RNAi, either exogenous addition or transcription in vivo, are known in the art (see Schubiger and Edgar, Methods in Cell Biology (1994) 44:697–713, and PCT application WO 99/32619, respectively), and are described in more detail below. In *C. elegans*, RNAi may be used to knock out a tumor suppressor gene in vulval precursor cells (Lu and Horvitz, Cell (1998) 95:981–991).

Construct Design for Increased Sensitizer Gene Expression or Activity

To model the effect of oncogene mutations in cancer cells, transgenic animals that express or overexpress known oncogenes, or homologs or orthologs of known oncogenes, can be generated. In this case, the sensitizer gene can be a wild type version of the oncogene that is overexpressed or an oncogene carrying an activating mutation. Expression of the sensitizer oncogene can be restricted to target tissues exactly as described above for the overexpression of a dominant negative tumor suppressor gene, using the construct of FIG. 6, where expression of the sensitizer oncogene is limited to cells in a target tissue where recombinase is expressed. A genetic strategy for Drosophila is depicted in FIG. 7 and detailed in Example 2. As with the dominant-negative construct, the oncogene construct allows the tissue that misexpresses the sensitizer gene to be recognized in adults due to the loss of the transformation marker.

In another embodiment, a tissue specific enhancer is used to directly drive overexpression of the dominant activated or wild type sensitizer oncogene in the target tissue or a dispensable portion, patch or domain thereof. In Drosophila, this can be accomplished using the construct design shown in FIG. 8, and the genetic strategy diagrammed in FIG. 9 and detailed in Example 3. A suitable construct for *C. elegans* is depicted in FIG. 11, and a screen using the construct is described in Example 4.

Abnormal Expression of Multiple Sensitizer Genes

Cancer cells often accumulate multiple alterations in their DNA. The screens described herein are amenable to isolating putative interactor genes that exhibit sensitizer gene-specific antiproliferation phenotypes in the presence of two or more simultaneously altered sensitizer genes in the same or different target tissues. For example, the FLP/FRT system (Golic and Lindquist, supra) can be used to generate mosaic patches of tissue that are homozygous for loss of function mutations in two different sensitizer genes.

In another embodiment, the FLP/FRT system can be combined with targeted expression of a sensitizer transgene using standard recombinant techniques. For example, eye tissue specific enhancers or promoters, such as eyeless or mirror in Drosophila, may be used to generate FLP-induced homozygous mutant patches of a first sensitizer gene in the eye and simultaneously overexpress a second sensitizer gene with a dominant negative mutation to produce an eye or a portion of the eye that is effectively "mutant" for two different cancer-related genes. In addition, two or more transgenes may be overexpressed in the same or different target tissues to better model the effect of multiple mutations in cancer.

Identification of Interactor Genes

Recombinant non-human metazoan animals having altered expression of a sensitizer gene in a target tissue, generated as described above, are hereinafter referred to as "sensitizer gene recombinants" or "SGRs". Once SGR animals have been generated, they are either subject to further mutation to induce mutations in putative interactor genes or they are crossed with animals that may contain mutated interactor genes.

Large-scale genetic modifier screens can be used to identify putative interactor genes in a non-targeted fashion. Using this approach, animals are subjected to mutagenesis to create gene deletions, insertions, or other mutations in a random fashion. Typically, chemical, radiation, or transposon mutagenesis is used.

In an alternative approach, genes that are believed to be possible interactor genes can be specifically targeted for mutagenesis. A variety of methods for targeted mutagenesis can be used including use of transposons, antisense, double-stranded RNA interference, peptide and RNA aptamers, directed deletions, homologous recombination, dominant negative alleles, and intrabodies.

With both of these approaches, which are discussed in further detail below, progeny of the mutagenized animals are screened to detect animals having a sensitizer gene-specific antiproliferation phenotype, indicating that an interactor gene has been mutated. Typically, the screens employ methods for detecting changes in tissue proliferation which, in a preferred embodiment, involves detection of the expression or lack of expression of a visible marker in a target tissue of the progeny of the SGR animal. The Examples section provides further detail on of how changes in tissue proliferation can be detected.

In a further embodiment of the invention, these screens can be performed in the presence of one or more anti-tumor agents or putative anti-tumor agents to identify compounds and interactor genes that act synergistically with each other.

Random Mutagenesis/Genetic Modifier Screens

A genetic modifier screen using invertebrate model organisms is a particularly preferred method for identifying putative interactor genes because large numbers of animals can be systematically mutagenized and screened, increasing the probability that new interactor genes will be identified. In *C. elegans* and Drosophila, a screen of up to about 10,000 animals is considered to be a pilot-scale screen. Moderate-scale screens usually employ about 10,000 to about 50,000 flies or up to about 100,000 worms, and large-scale screens employ greater than about 50,000 flies or 1,000,000 flies worms. Large-scale genetic modifier screens can also be performed in mice, however requires more resources, labor and time, making large-scale screens in invertebrates a more preferred choice. The use of genetic screens in Drosophila and *C. elegans* is outlined below. Greater detail is provided in Examples 1–5 which describe genetic screens in Drosophila, *C. elegans*, and the mouse.

In *C. elegans*, SGR hermaphrodites are typically exposed to a mutagen, such as EMS or trimethylpsoralen with ultraviolet radiation (Huang and Sternberg, Methods in Cell Biology (1995) 48:97–122). Alternatively, transposable elements can be used, oftentimes by the introduction of a mutator locus, such as mut-2, which promotes mobility of transposons (Anderson, Methods in Cell Biology (1995) 4:31–58). Progeny of the mutagenized animals are generated and screened for the rare individuals that display sensitizer gene-specific antiproliferation phenotypes. Any degree of reduced proliferation in the target tissue represents a possible interactor gene mutation. The most preferred antiproliferation phenotype is a cell-lethal phenotype.

Methods for performing genetic modifier screens in Drosophila are well-known (Wolfner and Goldberg, Methods in Cell Biology (1994) 44:33–80; and Karim et al., Genetics (1996) 143:315–329). The mutagenesis methods and other procedures used will depend upon the precise nature of the SGR flies and whether the putative interactor gene mutations to be detected are dominant or recessive. Specific examples of genetic modifier screens in Drosophila are described in Examples 1–3. In general, SGR flies are crossed with mutagenized flies. Preferably the animals used in the cross are inbred, which facilitates isolation of putative interactor genes that are identified in progeny of the cross. Progeny that exhibit sensitizer gene-specific antiproliferation phenotypes are immediately crossed to adults containing balancer chromosomes and used as founders of a stable genetic line. Additional secondary screens may be employed, as appropriate, to confirm the suitability of each new interactor gene mutant line for further analysis. Although the above-described type of Drosophila genetic modifier screen is quite powerful and sensitive, some putative interactor genes may be missed because the vast majority of mutations generated in the standard mutagenesis methods will be loss-of-function mutations. Gain-of-function mutations that result in the desired phenotype will be extremely rare. These types of mutations can be detected using a method of genetic screening described by Rorth et al. (Development (1998) 125:1049–1057), but it is expected that this approach will be used much less frequently than the genetic screens described above.

Targeted Mutagenesis

As an alternative to generating random mutations, mutations in putative interactor genes can be generated by any known method for targeted mutagenesis. This approach is useful to test whether a particular gene or family of genes, suspected of having interactor gene activity, exhibits the sensitizer gene-specific antiproliferation phenotype when mutated. It can also be used to confirm results obtained from a random mutagenesis/genetic screen in an organism that is the same or different from that used in the screen. Methods for targeted mutatgenesis of a variety of invertebrate and vertebrate model organisms are well known in the art (Ashburner, supra; "Fly pushing: The Theory and Practice of *D. melanogaster* Genetics" (1997) Cold Spring Harbor Press, Plainview, N.Y.; The nematode *Caenorhabditis elegans*, 1988, Wood, Ed., Cold Spring Harbor Laboratory Press, Cold Spring harbor, N.Y.; "Genetic Variants and Strains of the Laboratory Mouse" Third edition, 1996, Lyon, Rastqan, and Brown, ed., Oxford University Press).

Several methods for targeted mutagenesis are discussed below. In each case, SGR animals are subjected to targeted mutagenesis or are crossed with mutagenized animals. Progeny of the SGR animals are examined for sensitizer gene-specific antiproliferation phenotypes.

RNA-based methods: In *D. melanogaster* or *C. elegans*, loss of function phenotypes in putative interactor genes may be generated through RNA-based methods. Antisense RNA methods are described by Schubiger and Edgar (Methods in Cell Biology (1994) 44:697–713). One form of the antisense RNA method involves the injection of embryos with an antisense RNA that is partially homologous to the putative interactor gene. Another method involves expression of an antisense RNA that is partially homologous to the putative interactor gene. This can be achieved by operably joining a portion of the gene in the antisense orientation to a powerful promoter that can drive expression of large quantities of antisense RNA. Antisense RNA-generated loss of function phenotypes have been reported previously for several genes in both *D. melanogaster* and *C. elegans*.

Loss of function of putative interactor genes may also be generated by cosuppression, in which reduced gene expression is caused by expression or injection of a sense strand RNA corresponding to a partial segment of the putative interactor gene (Bingham, Cell (1997) 90(3):385–367; Smyth, Curr. Biol. (1997) 7(12):793–795; Que and Jorgensen, Dev. Genet. (1998) 22(1):100–109; Pal-Bhadra et al., Cell (1997) 90(3):479–90).

A preferred RNA-based method for generating loss of function phenotypes in putative interactor genes is by double-stranded RNA interference (dsRNAi) which has proven to be of great utility in genetic studies of *C. elegans* (see Fire et al., Nature (1998) 391:806–811), and can also be used in Drosophila (Kennerdell and Carthew, Cell (1998) 95:1017–1026; Misquitta and Patterson, PNAS (1999) 96:1451–1456). In one approach, dsRNA can be generated by transcription in vivo. In an alternative approach, complementary sense and antisense RNAs derived from a substantial portion of the coding region of the putative interactor gene, are synthesized in vitro. The resulting sense and antisense RNAs are annealed in an injection buffer, and the double-stranded RNA injected or otherwise introduced into animals. In *C. elegans*, dsRNAi can be administered by injection, soaking or feeding (Timmons and Fire, Nature (1998) 395:854; Montgomery et al., PNAS (1998) 95:15502–15507; Tabara et al., Science (1998) 282:430–431).

Peptide aptamers: Another method for generating loss-of-function phenotypes is the use of peptide aptamers, which are small polypeptides that act as dominant inhibitors of protein function. Peptide aptamers specifically bind to target proteins, blocking their function (Kolonin and Finley, Proc. Natl. Acad. Sci. (1998) 95:14266–14271). Peptide aptamers may be expressed in a controlled fashion by promoters that regulate expression in a temporal, spatial or inducible manner. Peptide aptamers act dominantly and thus can be used to analyze proteins for which loss of function mutants are not available. Peptide aptamers that bind to the protein product of a putative interactor gene can be isolated by a variety of techniques known in the art including isolation from phage libraries (Hoogenboom et al., Immunotechnology (1998) 4:1–20) or random peptide libraries using yeast two-hybrid screens (Xu et al., Proc. Natl. Acad. Sci. (1997) 94:12473–12478).

RNA apatamers: RNA aptamers are ligands for proteins that specifically inhibit protein function (Good et al., Gene Therapy (1997) 4:45–54; Ellington et al., Biotechnol. Annu. Rev. (1995) 1:185–214; Bell et al., J. Biol. Chem. (1998) 273:14309–14). Transgenic Drosophila lines expressing the desired aptamers may be generated by P element mediated transformation (Kolonin and Finley, Genetics (1998) 95:4266–4271).

Intrabodies: Intrabodies are intracellularly expressed single-chain antibody molecules designed to bind and inactivate target molecules inside cells. Intrabodies have been used in cell assays and in whole organisms including Drosophila (Chen et al., Hum, Gen. Ther. (1994) 5:595–601; Hassanzadeh et al., Febs Lett. (1998) 16(1, 2):75–80 and 81–86). Inducible expression vectors can be constructed with intrabodies that react specifically with the protein product of interactor genes.

Transposon mutagenesis: Transposable elements can be used to insert sequences into a putative interactor gene so that the encoded protein is not properly expressed. Techniques are well-established for the use of P element in Drosophila (Rubin and Spradling, Science (1982)

218:348–53; U.S. Pat. No. 4,670,388) and Tc1 in *C. elegans* (Zwaal et al., Proc. Natl. Acad. Sci. U.S.A. (1993) 90:7431–7435; and *Caenorhabditis elegans*: Modem Biological Analysis of an Organism (1995) Epstein and Shakes, Eds.). Other Tc1-like transposable elements are known including "minos" (U.S. Pat. No. 5,348,874), "mariner" (Robertson, Insect Physiol. (1995) 41:99–105), and "sleeping beauty" (Ivics et al., Cell (1997) 91(4):501–510). Additionally, transposable elements that function in a variety of diverse species, have been identified, such as piggyBac (Thibault et al., Insect Mol Biol (1999) 8(1): 119–23), hobo (Atkinson et al., Proc. Natl. Acad. Sci. U.S.A. (1993) 90:9693–9697), and hermes (O'Brochta et al., Genetics (1996) 142:907–914). P elements, or marked P elements, are preferred for the isolation of loss-of-function mutations in putative interactor genes in Drosophila because of the precise molecular mapping of these genes (Hamilton and Zinn, Methods in Cell Biology (1994) 44:81–94; and Wolfner and Goldberg, Methods in Cell Biology (1994) 44:33–80). Typically, modified P elements are used which contain one or more elements that allow detection of animals containing the P element. Most often, marker genes are used that affect the eye color of Drosophila, such as derivatives of the Drosophila white or rosy genes (Rubin and Spradling, supra; and Klemenz et al., Nucleic Acids Res. (1987) 15(10):3947–3959). However, any gene can be used as a marker that causes a reliable and easily scored phenotypic change in transgenic animals. Various other markers include bacterial plasmid sequences having selectable markers such as ampicillin resistance (Steller and Pirrotta, EMBO. J. (1985) 4:167–171); and lacZ sequences fused to a weak general promoter to detect the presence of enhancers with a developmental expression pattern of interest (Bellen et al., Genes Dev. (1989) 3(9):1288–1300).

A preferred method of transposon mutagenesis in Drosophila employs the "local hopping" method described by Tower et al. (Genetics (1993) 133:347–359). Each new P insertion line can be tested molecularly for transposition of the P element into the putative interactor gene by assays based on PCR. For each reaction, one PCR primer is homologous to sequences contained within the P element and a second primer is homologous to the coding region or flanking regions of the putative interactor gene. Products of the PCR reactions are detected by agarose gel electrophoresis. The sizes of the resulting DNA fragments reveal the site of P element insertion relative to the putative interactor gene. Alternatively, Southern blotting and restriction mapping using DNA probes derived from genomic DNA or cDNAs of the putative interactor gene can be used to detect transposition events that rearrange the genomic DNA of the gene. P transposition events that map to the putative interactor gene can be assessed for sensitizer gene-specific antiproliferation phenotypes.

In *C. elegans*, Tc1 transposable element can be used for directed mutagenesis of a putative interactor gene. Typically, a Tc1 library is prepared by the methods of Zwaal et al., supra and Plasterk (in *Caenorhabditis elegans*: Modern Biological Analysis of an Organism, Epstein and Shakes, eds., pp. 59–80) using a strain in which the Tc1 transposable element is highly mobile and present in a high copy number. The library is screened for Tc1 insertions in the region of interest using PCR with one set of primers specific for Tc1 sequence and one set of gene-specific primers and *C. elegans* strains that contain Tc1 transposon insertions within the putative interactor gene are isolated.

Gain of function/mis-expression: A preferred anti-cancer drug target is one that results in sensitizer gene-specific antiproliferation phenotype when its function is blocked. Thus, mutations of putative interactor genes typically will involve "knocking-out" gene function using one of the above-methods or any other suitable method for generating a loss of gene function. However, there may be some instances where mutations in interactor genes that result in over-expression or altered expression other than knock-out, will be beneficial. Recombinant methods are well-known in the art for generating such mutations. Notably, in Drosophila, binary control systems have been useful for generating mis-expression of genes in a wide variety of developmental stage-specific and tissue-specific patterns. Two examples of binary control systems include the UAS/GAL4 system (Brand and Perrimon, Devleopment (1993) 118(2):401–415) and the "Tet system" (Bello et al., Development (1998) 125:2193–2202), and both systems can be used in the practice of the present invention.

Characterization of Interactor Genes and Protein Product

Once an interactor gene is identified, it can be mapped and cloned using genetic and molecular methods known in the art. Interactor genes that come from a genetic screen in *C. elegans* are preferably mapped with visible genetic markers and/or with molecular markers such as STS markers (see The Nematode *Caenorhabditis elegans*, 1988, Wood, ed.; *Caenorhabditis elegans*: Modern Biological Analysis of an Organism, 1995, Epstein and Shakes, eds.) or SNPs (Zhao et al., Am J Hum Genet., (1998) 63:225–240). Interactor genes may be uncovered by identification of a genomic clone that reverses the sensitizer gene-specific antiproliferation phenotype. Alternatively, interactor genes that are identified by a Tc1-based screen can be uncovered using transposon display technology (Korswagen et al., PNAS (1996) 93(25):14680–14685). Interactor genes that are identified based on RNAi can be recovered by cloning the RNA or its encoding cDNA.

Standard techniques used for the mapping of interactor genes that come from a genetic screen in Drosophila include meiotic mapping with visible or molecular genetic markers; complementation analysis; and cytological analysis of chromosomal aberrations (Fly Pushing: Theory and Practice of Drosophila Genetics (1997), Greenspan, ed.; Ashburner, supra). Alternatively, interactor genes may be identified by positional cloning methods which include high resolution meiotic mapping, followed by mutation detection in candidate genes (e.g. Simon et al., Cell (1991) 67:701–716). Candidate genes can also be tested for their ability to reverse sensitizer gene-specific antiproliferation phenotypes via germline transformation.

Standard techniques used for mapping of interactor genes from a genetic screen in the mouse include linkage analysis to nearby genes (Pulst, Arch Neurol (1999) 56:667–672), use of radiation hybrid maps (Flaherty et al., Mamm. Genome (1998) 96:417–418), cytological analysis of chromosome aberrations by fluorescence in situ hybridization (FISH) (Trask, Trends Genet., (1991) 7:149–154; Shi et al., Genomics (1997) 45:42–47), and positional cloning (Collins, Clin Res., (1991) 39:615–623). Mapped genes can then be cloned using any suitable method, for example, rapid amplification of cDNA ends (RACE) (Frohman, PCR Methods App., (1994) 4:540–558), and long-range PCR (Wilton et al., Trends Genet (1996) 12:458).

Mutations in interactor genes may manifest phenotypes allowing for the testing of genetic interactions between interactor genes and other genes that may participate in the same, related, or interacting biochemical pathway(s). Genetic modifier screens as described above (but replacing the SGR animal with an animal having an interactor gene mutation and identifiable phenotype) can be used to identify genes that interact with the interactor genes. Examples of such screens in *C. elegans* and Drosophila are well-documented (Kayne and Stemberg, supra; Karim et al., supra; Go and Artavanis-Tsakonas, supra).

Interactor Gene Homologues and Orthologs

Once interactor genes have been identified, homologous genes in other species can be identified using cross-hybridization with interactor gene DNA probes and/or homology searches with sequence databases. For therapeutic applications in inhibiting tumor cell growth, and other proliferation disorders, human orthologs of the interactor genes are of particular interest. Once identified in other species, the orthologous interactor gene can be obtained from a suitable source such as a genomic or cDNA library. After amplification of a segment of an interactor gene ortholog using PCR or other suitable methods, that segment may be cloned and sequenced by standard techniques, and utilized to isolate a complete cDNA or genomic clone (Current Protocol in Molecular Biology, Vol. 1, Chap. 2.10, John Wiley & Sons, Publishers (1994); Sambrook et al., Molecular Cloning, Cold Spring Harbor (1989); Frohman, supra). The gene product can be isolated using standard methods (e.g. ion exchange, affinity, and sizing column chromatography; centrifugation; differential solubility). The amino acid sequence of the protein can be deduced from the nucleotide sequence of the chimeric gene contained in the recombinant. As a result, the protein can be synthesized by standard chemical methods known in the art (Hunkapiller et al., Nature (1984) 310:105–111). Alternatively, native interactor proteins can be purified from natural sources, by standard methods (e.g. immunoaffinity purification).

Methods known in the art can also be used for blocking gene function in cultured human and mouse cell lines having sensitizer gene mutations, including the use of antisense and intrabody technologies. The effect of blocking interactor gene function in tumor cell lines bearing a mutation in the sensitizer gene is compared to the effect on cell lines that are wild type for the sensitizer gene. A sensitizer gene-specific antiproliferative interaction will result in preferential arrested growth or killing of cell lines bearing a mutation in the sensitizer gene.

The ability of interactor genes and/or their protein products to induce sensitizer gene-specific antiproliferation can be confirmed using cell-based systems. Recently, RNAi has been successfully used in cultured Drosophila cells to inhibit expression of targeted proteins (Dixon lab, University of Michigan, http://dixonlab.biochem.med.umich.edu/protocols/RNAiExperiments.html). Thus, cells having sensitizer gene mutations that result in altered expression, and, in some cases, abnormal proliferation, can be subject to RNAi targeted to inhibit interactor gene function and changes in sensitizer gene-specific antiproliferation can be observed. A suitable protocol is described in Example 6.

In another embodiment, RNAi-mediated inactivation of genes in cultured cells can be used to directly screen for and identify interactor genes that cause sensitizer gene-specific antiproliferation. The strategy for this type of tissue culture based screen in Drosophila cells is outlined in Example 7.

Identification of Compounds that Modulate Interactor Gene Function

Compounds that specifically bind to or otherwise alter the activity of an interactor gene or its gene product may have therapeutic utility and can be evaluated for antiproliferative effects on cells or organisms that have altered expression of a sensitizer gene. Proteins and other compounds that bind to, or otherwise directly interact with, the interactor genes and proteins may be candidates for pharmaceutical agents and can be identified by screening methodologies that are well known in the art (see e.g., PCT International Publication No. WO 96/34099). Any variety of exogenous compounds, both naturally occurring and/or synthetic (e.g., libraries of small molecules or peptides, or phage display libraries) may be screened for binding capacity. For example, the purified interactor gene product or fragment thereof can be used as an immunogen to generate monoclonal or polyclonal antibodies which are then tested for their ability to reduce tumor formation caused by sensitizer gene mutations.

Compounds that exhibit sensitizer gene-specific antiproliferation may be assayed using cell culture. Identification of small molecules and compounds as potential pharmaceutical compounds from large chemical libraries requires high-throughput screening (HTS) methods (Bolger, Drug Discovery Today (1999) 4:251–253). Any cell line that exhibits uncontrolled proliferation caused by abnormal expression of a sensitizer gene can be used. Preferably the cell line is a human tumor cell line.

In another method of identifying anti-tumor compounds, varying doses of one or more test compounds are administered to SGR animals. Potential anti-tumor compounds are identified as those compounds tested that specifically inhibit proliferation of the target tissue having modified expression of the sensitizer gene(s), and which have no other adverse affects on the animal. In a preferred embodiment of this method, the SGR animal used in the compound screen is *C. elegans*. Typically, the compounds to be tested are dissolved in DMSO or other organic solvent, mixed with a bacterial suspension at various test concentrations, preferably OP50 strain of bacteria (Brenner, Genetics (1974) 110:421–440), and supplied as food to the worms. The population of worms to be treated can be synchronized larvae (Sulston and Hodgkin, in The nematode *C. elegans* (1988) Wood, Ed., Cold Spring Harbor Laboratory Press, Cold Spring harbor, N.Y.) or adults or a mixed-stage population of animals. Adult and larval worms are treated with different concentrations of compounds, typically ranging from 1 mg/ml to 0.001 mg/ml. Antiproliferation phenotypes are examined in both acutely and chronically treated adult and larval worms. For the acute assay, larval and adult worms are examined immediately after application of the compound and re-examined periodically (every 30 minutes) for 5–6 hours. Chronic or long-term assays are performed on worms and the behavior of the treated worms is examined every 8–12 hours for 4–5 days. In some circumstances, it is necessary to reapply the compound to the treated worms every 24 hours for maximal effect.

In another embodiment, the SGR animal used in the compound screen is Drosophila. Putative anti-tumor agents can be administered to insects in a variety of ways, including orally (including addition to synthetic diet, application to plants or prey to be consumed by the test organism), topically (including spraying, direct application of compound to animal, allowing animal to contact a treated surface), or by injection. The first step in an insect assay is usually the determination of the minimal lethal dose (MLD) on the insects after a chronic exposure to the compounds. The compounds are usually diluted in DMSO, and applied to the food surface bearing 0–48 hour old embryos and larvae. Once the MLD is determined, more specific acute and chronic assays can be designed. In a typical acute assay, compounds are applied to the food surface for embryos, larvae, or adults, and the animals are observed after 2 hours and after an overnight incubation. For a chronic exposure assay, adults are placed on vials containing the compounds for 48 hours, then transferred to a clean container and observed for antiproliferation phenotype.

In another preferred method of identifying anti-tumor compounds, a putative inhibitor of interactor gene function is administered to immunodeficient mice bearing xenografts of human tumor cells having sensitizer gene mutations that result in abnormal proliferation. In this case, the xenograft is considered the equivalent of the "target tissue" of an SGR animal. The use of mouse xenografts in the evalutation of possible chemotherapeutics is well known (see review by Taghian and Huang, Cancer Chemo. and Pharm. (1997) 40(3):209–214; Steel and Peckham, Brit. J. Cancer (1983) 47: 1–13; and Tveit et al., Br. J. Cancer (1980) 41:724–733).

EXAMPLES

The following examples are provided merely as illustrative of various aspects of the invention and shall not be construed to limit the invention in any way.

Example 1

Screen to Identify Interactor Gene Mutations in Drosophila that Specifically Kill Cells Lacking Rb Function Preparation of Dominant Transformation Construct:

A mutation that reduces or eliminates expression of the Rbf gene, which is the Drosophila homolog of the retinoblastoma gene and is located on the X chromosome, was used in these studies (see Du and Dyson, supra). This gene was selected because the human orthologue has a high frequency of mutations in human tumors and also because Drosophila Rbf mutations themselves are not lethal to the fly.

A "flip-out" Rbf rescue construct, was constructed with the features depicted in FIG. 2A. The insertion sequences (IS), located at the left and right ends of the construct, comprised P-element insertion sequences that cause germline transformation (Rubin and Spradling, supra). The recombinase target sites (R) comprised two FRT direct repeat sequences (Golic and Lindquist, supra) arranged in a head-to-tail orientation just downstream of the left insertion sequence, and upstream of the right insertion sequence, as shown in FIG. 2A. Between the recombinase sequence were three genes: a gene encoding the site-specific recombinase (SR), FLP, which recognizes the FRT sequences (Golic and Lindquist, supra); a fragment of genomic DNA that provides wild-type expression and function of the Rbf gene (i.e. the sensitizer gene (SG)); and a white (w+) gene that serves as a marker (M) for transformation. The w+ gene is the gene that results in the wild-type red eye color in Drosophila. The FLP recombinase was placed under the regulation of the eyeless enhancer/promoter, such that in eye tissues where the eyeless promoter is active, the FLP recombinase will be expressed, and the three genes between the recombinase target cites will be excised, as shown in FIG. 2B. The recombinase gene (SR) is also deleted to prevent possible chromosome instability due to recombinase activity at the remaining target site.

Preparation of Drosophila with Altered Rb Activity in Eye Tissue:

The Rbf rescue construct was injected into Drosophila YW (yellow-white, Ashbumer, supra) embryos using standard procedures (Rubin and Spradling, supra). In adult flies, successful transformants were identified as having red pigment in eye tissue where the eyeless enhancer/promoter is not active, and white, hyperproliferative tissue in eye tissue in which the eyeless enhancer/promoter is active due to excision of the marker and the Rbf gene.

An Rbf "flip-out" transgene insertion on the X chromosome was recovered, and this transgene insertion was then recombined onto a w$^-$/Rbf$^-$X chromosome. This recombinant chromosome was used to establish a screening stock that constitutively produces patches of white, hyperproliferative (w$^-$/Rbf$^-$) tissue in the eye. Greater than 99% of the animals in the stock produced w$^-$/Rbf$^-$ patches in the eyes of the progeny, without much variation in the size of the patches. Homozygous females and hemizygous males of this stock were viable and fertile due to the presence of the Rbf$^+$ transgene in all tissues except the eye disc.

Screen to Identify Mutant Interactor Genes that Inhibit Proliferation of Rbf$^-$ Eye Tissue:

FIG. 4 depicts a genetic strategy for identifying mutations on chromosomes 2 and 3 that result in specific, dominant inhibition of proliferation of cells lacking Rb function. Females from the screening stock, Rbf "mosaic" females, were crossed to male flies that had been mutagenized using EMS (Amano and Smith, Mutat Res (1965) 2:344–51). The females' X chromosome contained the Rbf rescue construct described above. The females' second chromosome contained the sp gene that causes a speckled body phenotype, and the third chromosome contained the e gene, which causes an ebony body phenotype. The sp and e genes were used as visible markers for linkage analysis.

The mutagenized males were w$^-$ on the X chromosome, and thus had the white-eye phenotype, and had isogenized second and third chromosomes.

The male F1 progeny were screened for possible mutagenized interactor genes (designated by an asterisk (*) in FIG. 4) on the second and third chromosomes by identifying progeny that had reduced-size or absent white patches of eye tissue. F1 males scoring positive for the sensitizer gene-specific antiproliferation phenotype were backcrossed to the maternal F0 genotype to retest the phenotype, i.e. to assure that the phenotype remained consistent after the cross. For consistent phenotypes, the segregation of the mutation was scored relative to speck and ebony to determine chromosome linkage. Each interactor gene mutation was then balanced over an appropriate balancer chromosome such as CYO (Curly of Oster) or TM3 (Third Multiple 3, on chromosome 3) to create a stock line. The balancer chromosome contains multiple inversions and markers to facilitate crossing schemes due to ease of detection, and also suppresses recombination between homologs.

100,000 flies were screened, resulting in several possible candidate interactor genes. Backcrossing yielded 1 consistent sensitizer gene-specific antiproliferation phenotype. These results demonstrate the rigorous sensitivity and selectivity of the screen.

FIG. 5 depicts a genetic strategy for identifying Rb sentizer gene-specific antiproliferation mutations on chromosomes X, 2, and 3. Mutagenized male F0 flies are produced exactly as described above. The mutagenized F0 males are crossed to F0 females bearing a compound X chromosome (i.e., the X chromosomes are attached; Greenspan, supra) marked with yellow and forked marker genes, a Y chromosome, a second chromosome marked with speck (Sp) and a third chromosome marked with ebony (e) marker genes. The compound X and the Y chromosomes in the F0 female force patriclinous inheritance of the mutagenized X chromosome from the F0 male. The male F1 progeny are screened for possible mutagenized interactor genes ("*") on the X, second, and third chromosomes by screening for a reduction or absence of white eye tissue. F1 males scoring positive for putative interactor genes are backcrossed to the maternal genotype to retest the phenotype. If the phenotype retests, the segregation of the mutation is scored relative to speck and ebony to determine chromosome linkage. If X-linked, all male progeny will display the phenotype. The mutation is then placed over an appropriate balancer such as FM6 or FM7 for X chromosome, CYO for $2^{nd}$ chromosome, and TM3 for third chromosome, and stocked.

Example 2

Screen to Identify Dominant Interactor Gene Mutation in Drosphila that specifically kill Cell with a Constitutively Activated Ras Gene Preparation of a Transformation Construct:

A mutation that results in constitutive activation of the Drosophila ras gene ($ras^{act}$) has been described (Fortini et al., supra). A $ras^{act}$ transformation construct is made as outlined in FIG. 6A. Insertion sequences (IS), recombinase target site (R), site specific recombinase (SR) under the control of the eyeless promoter, and the marker gene (M) are as described above in Example 1 with reference to FIG. 2A. In addition, there is a promoter sequence (P) between the left insertion sequence and recombinase target site, and a transcription termination/polyadenylation sequence (T) at the right end of the left recombinase target site that prevents promoter activity. Preferred promoters and transcription termination sequences for this construct are from the actin and tubulin genes (Struhl and Basler, Cell (1993) 72:570–540; Basler and Struhl, Nature (1994) 368:208–214). In contrast to the construct depicted in FIG. 2A, where an activated sensitizer gene is located between the recombinase target sites, the construct of FIG. 6A has an inactive sensitizer gene located downstream of the 3' recombinase target site. For example, a 2 kb fragment of genomic DNA that encodes the $ras^{act}$ gene but lacks promoter or enhancer elements could be used (Fortini et al., supra).

This transformation construct is injected into embryos. When recombinase is expressed due to activity of the tissue-specific promoter in the developing eye, the sequences between the recombinase target sites are excised so that the promoter sequence becomes juxtaposed next to the dominant activated sensitizer rendering the sensitizer gene active ($SG_A$), as depicted in FIG. 6B. Transgenic animals will constitutively express $ras^{act}$ in white patches of cells in the developing eye.

Screen for Sensitizer Gene-specific Antiproliferation Mutations:

Animals transformed with the above-described construct are crossed with mutagenized males using the genetic strategy outlined in FIG. 7. In this example, interactor gene mutations are screened that induce sensitizer gene-specific antiproliferation in cells misexpressing a constitutively activated ras gene. Male F0 flies bearing a w⁻X chromosome and isogenized second and third chromosomes are crossed to female F0 flies bearing a w⁻X chromosome, a balancer chromosome (e.g. CyO) having the $ras^{act}$ transformation construct described above and marked with Sp (Sternopleural), and a third chromosome bearing the ebony marker gene. Referring both to the construct in FIG. 6A and the diagram in FIG. 7, respectively, an actin promoter (P or Pact) is separated from the $ras^{act}$ sensitizer gene ($SG_I$ or $ras^{act}$) by two FRT recombination sites (R or >) which are in turn separated by the white⁺ gene (M or w+) and a FLP recombinase gene driven by the eyeless promoter (SR or ey-FLP). FLP activity in the eye causes excision of the white and FLP genes and activates expression of the $ras^{act}$ gene from the actin promoter. The male F1 progeny are screened for possible mutagenized interactor genes ("*") by screening for sensitizer gene-specific antiproliferation activity manifested by reduced-size or absent white patches of eye tissue relative to the size of the white patches of eye tissue in the F0 females. F1 males scoring positive for putative interactor gene activity are backcrossed to the maternal F0 genotype to retest the phenotype. If the phenotype retests, the segregation of the mutation is scored relative to Sternopleural and ebony to determine chromosome linkage. The mutation is then placed over an appropriate balancer chromosome and stocked.

Example 3

Screen to Identify Recessive Mutations in Drosophila Interactor Genes that Specifically Kill Cells with a Constitutively Activated Ras Gene Preparation of Transformation Construct:

An alternative construct that can be used to identify dominant interactor gene mutations in Drosophila that specifically kill cells with a constitutively activated Ras gene is depicted in FIG. 8. Two minimal promoters (P) (e.g. from the hsp 70 gene) facing in the opposite orientations flank one or more copies of a tissue-specific enhancer element (E), such as the enhancer from the mirror gene (McNeill et al., Genes and Development (1997) 11:1073–1082), which specifically drives expression in the dorsal sector of the eye. The enhancer element (E) drives tissue-specific expression from both promoters. One of the promoters drives expression of the sensitizer gene (SG), while the other promoter drives expression of a marker gene (M), e.g., the white⁺ gene. The white⁺ gene, which produces red eye pigment, serves as both a marker for transformation as well as a marker for the cells expressing the sensitizer gene (SG) (e.g. an activated oncogene such as ras ($ras^{act}$), dominant negative tumor suppressor gene or an RNAi molecule to inactivate an endogenous tumor suppressor gene activity). Other marker genes can also be used, such as GFP. The eye cells not expressing the sensitizer gene and which exhibit normal expression of ras, are w⁻ and thus unpigmented.

Screen for Sensitizer Gene-specific Antiproliferation Mutations:

FIG. 9 diagrams a screening method employing the above construct. Sensitizer gene recombinant female flies are crossed with male flies that have been mutagenized. Progeny containing putative interactor genes that have been mutated and result in sensitizer gene-specific antiproliferation phenotype are identified by a reduction or loss of the pigmented patch in the dorsal sector of the eyes.

The screens described thus far rely on the isolation of mutations in interactor genes that when heterozygous mutant (i.e., act dominantly), cause sensitizer gene-specific antiproliferation activity of cells expressing the sensitizer gene. A screen for identifying recessive mutations that induce sensitizer gene-specific antiproliferation activity in cells misexpressing a constitutively activated ras gene is diagrammed in FIGS. 10A and 10B and utilizes the construct described above. Mutant interactor genes may be embryoniclethal as homozygotes. To circumvent early organismal lethality, clonal populations of cells homozygous mutant for the putative interactor gene can be generated in an otherwise heterozygous interactor mutant animal. Referring to both FIGS. 10A and 10B, male flies carrying the FRT target site for the FLP site-specific recombinase at the base of the chromosome arms (Xu and Rubin, Development (1993) 117:1223–1237) are mutagenized and crossed to females. The genetic background of the female flies is engineered such that the sensitizer gene is expressed in the dorsal domain of cells under control of the mirror enhancer element/promoter (mirror-S) and are marked due to the production of red eye pigment in the dorsal domain from the white gene. In this example, the cells in the ventral sector of the eye lack sensitizer gene expression and appear white due to absence of the white gene. The female flies also carry a transgene which expresses the FLP site-specific recombinase under the control of the eyeless enhancer/promoter (Ey-FLP), FRT sites at the base of the same chromosome arms, plus a dominant cell lethal (CL) gene expressed under control of the eye-specific glass multimer response elements (GMR-CL) (Stowers and Schwarz, Genetics (1999) 152:1631–1639), or alternatively a Minute mutation (Golic MM and Golic KG, Genetics (1996) 143:385–400) on the same arm as the FRT site. Examples of CL genes include the apoptotic activators reaper (White et al., Science (1994) 265:677–683), hid (Grether et al., Genes & Develop. (1995) 9:1694–1708), and grim (Chen et al., Genes Devel. (1996) 10:1773–1782). The diagram of the genetic cross is presented in FIG. 10B. The eyeless-FLP transgene drives somatic recombination in mitotically active eye cells via the FRT sites. The somatic recombination of the chromosome arm results in the generation of clonally derived eye cells that are homozygous mutant for the interactor gene.

In the reciprocal recombination event, eye cells are generated that are homozygous for the GMR-CL transgene and therefore die during later stages of eye development. Similarly, eye cells that do not undergo the recombination event remain heterozygous for the GMR-CL and also die. Since GMR-CL results in eye-specific cell lethality, the only cells able to survive and populate the eye tissue are those cells homozygous mutant for the interactor mutation. A mutation in a gene that by itself kills the cells or causes cell cycle arrest, will fail to produce any eye tissue and therefore can be identified and discarded because these mutations will result in flies that have no eyes (FIG. 10A). The progeny of the cross are then scored for the specific absence of the marked or "mutant" ($w^+$, $ras^{act}$ expressing) cells of the dorsal domain in the eye, indicating that a homozygous mutation in an interactor gene has resulted in lethality of those cells with altered sensitizer gene expression. A bonafide sensitizer gene-specific antiproliferation mutation in an interactor gene should not cause lethality of the unmarked ventral domain of cells, which lack sensitizer gene expression. These putative interactor mutations are retested and those that pass the retest are mapped to a chromosome and crossed with an appropriate balancer to create a stock line.

Example 4

Screen to Identify Mutations in C. Elegans Interactor Genes that Specifically Kill Cells with a Constitutively Activated Oncogene, or a Dominant Negative Tumor Suppressor Gene Preparation of Transformation Construct and Generation of Screening Stock:

Transformation constructs containing as the sensitizer gene (SG) a constitutively activated ras ($ras^{act}$) (ras let-60; Eisenmann and Kim, supra), and an in-frame GFP marker gene (Chalfie et al., Science (1994) 263:802–805) are prepared using the construct design outlined in FIG. 11. $Ras^{act}$ is placed under the control of the lin-31 promoter/enhancer, which is active specifically in the vulval precursor cells. A 3' UTR from the unc-54 gene is used for polyadenylation and message stability (Fire et al., Gene (1990) 93:189–198). SGR animals are prepared by injecting the transformation construct into the hermaphrodite gonad (N2 worms, Bristol, http://elegans.swmd.edu) to obtain transgenic lines that constitutively express $ras^{act}$ in the vulval precursor cells. A coinjection marker, pRF4, which causes a dominant roller phenotype (Mello et al., EMBO (1992) 10:3959–3970), is also injected. Transformed worms express $ras^{act}$ in the vulval precursor cells resulting in a change in vulval morphology, such as a multivulva or protruding vulva phenotype, indicating hyperproliferation of vulval precursor cells. At this stage, animals may be selected for further study based on vulval morphology, or optionally, the phenotype of the animals may be enhanced as discussed further below.

The vulva precursor cell division can be studied via cell lineage analysis, using both Nomarski differential interference-contrast and fluorescence imaging microscope. The vulval precursor cells, which undergo three rounds of cell division during development, are distinct from neighboring cells in their morphology. The green fluorescence emitted by GFP provides another marker for vulval precursor cells. Animals are chosen that exhibit abnormal vulva morphology, exhibit the roller phenotype, and fluoresce green in the vulval tissue. These criteria should be present in >90% of the animals as a sign of successful transformation.

Optionally, the phenotype of the animals may be enhanced by crossing into a lin-12 gain of function phenotype (n137 gf). In lin-12 (n137 gf) worms, the six vulval precursor cells adopt secondary vulva fates regardless their positions, and give rise to six pseudovulva. If there is extra cell division of vulval precursor cells, each of the extra daughter cells of vulval precursor cells has the capacity to adopt a secondary fate and generate a pseudovulva (Hong et al., Development (1998) 125:3585–3597). To determine if there is an extra cell division, SGR animals are crossed into lin-12 (n137) background. If the animals display 12 pseudovulva it can be concluded that there is one extra cell division in vulval precursor cells. Again, if >90% of the animals show the abnormal vulval morphology, exhibit the roller phenotype, and fluoresce green in the vulval tissue, a successful transformation has occurred, and the screen may be continued.

Screen for Sensitizer Gene-specific Antiproliferation Mutations:

SGR hermaphrodites are chemically mutagenized with EMS or ENU. Hermaphrodites with the rolling phenotype, are identified one or two generations later that do not contain vulval cell hyperproliferation phenotypes, and do not show the GFP expression.

Unlike Drosophila, the transgenes do not integrate into the genome, but recombine to form a semi-stably inherited extrachromosomal array. The variable inheritance of the arrays enables a quick comparison of the vulval phenotype in siblings with and without the lin-31 driven sensitizer gene. The mutant worms are cloned to a separate plate and their progeny are scored to confirm the phenotype. Among the self-progeny of the hermaphrodite will be animals that have lost the transgenic array during meiosis. These animals will be scored for abnormal vulval morphology. Mutants of interest will kill or slow the proliferation of cells that express activated ras, but will not affect the development of cells that express the wild type, endogenous, ras gene.

Example 5

Screen to Identify Mutations in Mouse Interactor Genes that Specifically Kill Cells with a Constitutively Activated Ras Gene Preferred strains of mice for these experiments are C57B16 and Balb C., which can be obtained from Charles River Laboratories (http://www.criver.com/1999rm/htdocs/stocks.html), Jackson laboratories (http://www.jax.org/), or Taconic (http://www.taconic.com/index.htm. For the examples mentioned here, putative interactor genes are mutated using ENU chemical mutagenesis (Russell et al., Proc. Nat. Acad. Sci. USA (1982) 79:3589–3591).

Mouse Screens Based on Knockout of a Tumor Suppressor Gene

As depicted in FIG. 12, a tumor suppressor gene construct, p16Ink4 (Serrano et al., supra) is made having flanking FRT sites (Vooijs et al., Oncogene (1998) 17:1–12). Standard techniques for homologous recombination are used to insert the construct into mouse embryonic stem cells to generate transgenic mice that are homozygous for the constructs. Transgenic mice are also made with one copy of a construct comprising an IRES element (Wimmer and Nomoto, Biologicals (1993) 21:349–356) and the BMP5 promoter (DiLeone et al., supra) operably linked to sequences encoding FLP recombinase and GFP. The two types of transgenic mice are crossed. In the ear cartilage of progeny SGR mice, FLP recombinase will induce recombination of the FRT sites and deletion of the p16 gene, thereby providing a tissue-specific knockout of gene function resulting in hyperproliferation of ear cartilage. Recombinase expression can be identified by detection of GFP.

Female SGRs from this stock are crossed to mutagenized male mice that are homozygous for the tumor suppressor-flanked FRT, as depicted in FIG. 12. Progeny mice are observed for changes in ear cartilage, such as a misshapen ear, due to death of the cartilage cells of the ear where the p16 gene is knocked out. Such mice are identified as potentially having interactor gene mutations that specifically inhibit proliferation or kill cells lacking sensitizer gene function. In a litter with progeny exhibiting the ear phenotype, it is expected that 50% of the siblings should have loss of p16 and FLP (or presence of FRT sites), in addition to the ear phenotype. The genotype may be tested by PCR on the tail. These progeny are retested by back-crossing to the parental genotype. A true interactor mutation in the F2 progeny will exhibit the misshapen ear phenotype, and the presence of FRT sites (or loss of FLP-e:::GFP, and p16).

Mouse Screens Based on a Dominant Negative Mutation of a Tumor Suppressor Gene:

Referring to FIG. 13, a construct can be made comprising the dominant negative allele of p53, p53 Arg273His, operably linked to the TRP-1 promoter which is specifically active in melanocytes (Nylander et al., gi|5852319|gb|AF087673.1). Pronuclear injection is used to produce C57B16 transgenic lines carrying the construct (Gordon and Ruddle, Methods Enzymol (1983) 101:411–433; U.S. Pat. No. 5,780,236). C57B16 mice, which are normally black. p53-specific antibody staining on skin tissue samples is used to confirm the presence of the transgene in the animals. Alternatively, the construct may contain a marker gene such as GFP, that can be visually detected. Females from this line that are homozygous for the construct are crossed with mutagenized male C57B16 mice. Progeny of this cross carry one copy of the construct. Progeny having lighter skin than the parent mice potentially have mutations in interactor genes that cause sensitizer gene-specific antiproliferation. A change in coat color from black to albino is indicative of death of melanocytes.

Mouse Screens Based on Overexpression of an Oncogene:

Referring to FIG. 14, a transformation construct is made comprising the T-cell specific Lck promoter (Wildin et al., J Immunol (1995) 155(3):1286–1295) operably linked to a hyperactive, oncogenic allele of the ras gene, ras Gly12Val (Trahey and McCormick, supra). The construct may also include an IRES element and a marker gene such as GFP. This construct is used to generate SGR mice that have overproliferation of T cells. Females of this line that are homozygous for the construct are crossed with mutagenized male mice. The progeny are bled at about 3 weeks of age. Mutations that lead to reduced proliferation or T-cell death are detected by analysis of blood samples using fluorescence-activated cell sorting (FACS), and CD4/CD8 markers, or by lack of GFP expression.

Genetic Strategy

Sensitizer gene-specific antiproliferation screens using the mouse lines described above can be either first generation screens (diagrammed in FIG. 15A) looking for dominant mutations that cause reduction or killing of the target tissue, or three generation recessive screens (diagrammed in FIG. 15B) that detect recessive mutations in interactor genes that cause sensitizer gene-specific antiproliferation. Referring to FIG. 15A, in a first generation screen, the SGR female mice containing the construct described above are crossed with mutagenized $G_0$ mice. $G_1$ progeny are scored for sensitizer gene-specific antiproliferation, as determined by reduced T cell levels.

To detect interactor genes that require mutations in both copies of a gene for sensitizer gene-specific antiproliferation, a three generation recessive screen can be used (Hentges et al., Development (1999) 126:1601–1609; Kasarkis et al., PNAS (1998) 95:7485–7490). SGR female mice containing the construct described above are crossed with mutagenized male mice. $G_1$ male progeny are then crossed to the SGR females homozygous for the LCK-ras$^{act}$ transgene. $G_2$ female progeny carry a single copy of the LCK-ras$^{act}$ transgene and mutated interactor gene, if any, that was present in the father. To generate $G_3$ progeny carrying two copies of the interactor gene mutation, the $G_2$ females are superovulated at 6–8 weeks of age and mated to their fathers. $G_3$ progeny are analyzed for the sensitizer gene-specific antiproliferation phenotype (loss of T cells). One half of the $G_3$ progeny will carry the LCK-ras$^{act}$ transgene. Presence of the transgene can be determined by PCR or hybridization using a DNA sample taken from the $G_3$ mprogeny.

To facilitate mapping of mutations recovered in this screen, the initial mutagenized male is a different inbred strain than the females used in the first and second crosses. In this example, the mutagenized $G_0$ males are C57BL/6J and the females are C3H/HeJ. To map and identify any gene mutations identified in the sensitizer gene-specific antiproliferation screen, mice carrying the mutation are crossed to C3H/HeJ mice carrying the LCK-ras$^{act}$ transgene and the progeny are back-crossed or inter-crossed. Progeny from the back-cross or inter-cross are analyzed for the sensitizer gene-specific antiproliferation phenotype and for a series of polymorphic markers spanning the genome that distinguish the C57BL/6J and C3H/HeJ DNA. C57BL/6J markers that co-segregate with the sensitizer gene-specific antiproliferation phenotype identify the chromosomal region containing the mutation causing the sensitizer gene-specific antiproliferation phenotype.

Example 6

Confirmation of Sensitizer Gene-specific Antiproliferation Effects Using dsRNAi in Cell Lines RNAi can be used to confirm sensitizer gene-specific antiproliferation effects. Interactor genes identified using the methods of any of Examples 1–5 are cloned and sequenced using standard methods. Primers containing an upstream T7 RNA polymerase binding site and downstream target gene sequences are designed. For each interactor gene, two primers are designed: forward and reverse, with a T7 site, separated by about 0.7–1 kb. Typically, the 5' end of the gene used, including a large majority of the coding region. In some instances, the use of multiple target PCR products may improve results (e.g., 5' and 3' templates). PCR reaction is then performed, preferably using EXPAND High Fidelity (Boehringer Mannheim, Indianapolis, Ind.). For a previously cloned target gene, 25 cycles is sufficient with 100 ng vector. PCR products are then purified.

Preparation of the dsRNA template: An RNA transcription reaction is performed using the Promega Large Scale RNA Production System (Madison, Wis.) following manufacturer's protocols. Ethanol precipitation of RNA is performed and the RNA is annealed by a first incubation at 68° C. for 10 min, followed by a second incubation at 37° C. for 30 min. The resulting dsRNA is stored at −80° C.

RNAi experiment in tissue culture: Drosophila Schneider cells, other Drosophila cell lines, or cell cultures established from Drosophila organs or developmental stages (e.g. imaginal disks) may be used. Test cells, engineered to have abnormal sensitizer gene expression, and normal, control cells are used. Cells are harvested, counted to assess concentration, and resuspended in DES Serum-free Expression medium (Invitrogen, Carlsbad, Calif.) with 2 mM glutamine at a concentration of $1 \times 10^6$ cells/mL. 1 mL aliquots of cells are added to each well of a 6-well tissue culture plate, followed immediately by 15 $\mu$g dsRNA. After an incubation of 30–60 min at room temperature, 2 mL normal medium (Gibco Drosophila Schneider cell medium, supplemented with 10% serum, pen/strep—Gaithersburg, Md.) are added and the cells are incubated at 25° C. for approximately 72 hrs. Cells are harvested and assays are performed to test for loss of interactor gene product or RNA by appropriate assays. If RNAi is successful, control and test cells are compared to test for antiproliferation effects, for example by Trypan Blue staining and counting. Reduced proliferation or lethality of test cells and not control cells indicates sensitizer gene-specific antiproliferation.

Example 7

Screen to Identify Sensitizer Gene-specific Antiproliferation Genes Using dsRNA-mediated Interference (RNAi) in Drosophila Tissue Culture Cell Lines:

The observation that RNAi can be used to specifically and selectively inactivate one or more genes simultaneously in Drosophila tissue culture cells provides an additional means of screening for interactor genes that have sensitizer gene-specific antiproliferative activity when they are inactivated. In this screen the inactivation of the interactor gene is mediated by RNAi, which would mimic the function of drug that specifically inactives that gene function. The procedure for carrying out RNAi in Drosophila tissue culture cells outlined above in Example 6 can be carried out on a large scale such that part or all the genes in the Drosophila genome could be inactivated by RNAi and tested as potential interactor genes. In order to carry out this type of RNAi-mediated screen in tissue culture cells, a library of double stranded RNAi molecules directed against part or all of the genes in the Drosophila genome would be constructed as outlined in FIG. 16. From the complete Drosophila genome sequence and Expressed Sequence Tags (ESTs) an RNAi library is constructed by in vitro transcription from convergently oriented T7 promoters (see Example 6 for details). The sense and antisense RNA strands are annealed and arrayed into 96-well plates with each well containing a different RNAi molecule directed against a different gene in the genome.

FIG. 17 schematically shows how one would carry out a screen for sensitizer gene-specific antiproliferation genes using RNAi in Drosophila tissue culture cell lines.

An aliquot of Drosophila tissue culture cells (e.g. S2 cells) is placed in each well of a 96-well plate. To each well of cultured cells, an aliquot of each of the 96 different dsRNA from the RNAi library is added to a different well containing the Drosophila cells. In this way each well of the 96 well plate contains a different RNAi molecule directed against a different gene in the genome. Inactivation of the sensitizer gene that is a tumor suppressor gene could be achieved by the use of an RNAi molecule directed against that tumor suppressor gene. This sensitizer gene-specific RNAi molecule would be aliquoted into each of the 96 wells containing the Drosophila cells and the 96 different RNAi molecules directed against potential interactor genes. Thus, in this way one would simultaneously inactivate both the sensitizer gene and the potential interactor gene by RNAi. If the sensitizer gene is an oncogene, then the activated form of the oncogene could be expressed in Drosophila tissue culture cells under the control of a constitutive promoter or an inducible promoter and introduced by cell transfection. Following the introduction of the RNAi library to the cultured cells, the cells are then assayed for sensitizer gene-specific antiproliferation effects as described in Example 6. Here again, reduced proliferation or lethality of test cells and not control cells indicates that the RNAi molecule directed against that interactor gene is causing sensitizer gene-specific antiproliferation.

What is claimed is:

1. A method of identifying an anti cell proliferation drug target comprising:
    (a) providing a Drosophila or *C. elegans* that has been recombinantly modified to have altered expression of one or more sensitizer genes wherein the sensitizer gene or genes is selected from the group consisting of a tumor suppressor gene, an ortholog of a tumor suppressor gene, an oncogene, and an ortholog of an oncogene, limited to a portion of a target tissue dispensable for viability, wherein said limited portion of the target tissue is identifiable by presence or absence of expression of a marker gene;
    (b) generating progeny of the Drosophila or *C. elegans* that have mutations in, reduced expression, expression of putative interactor genes;
    (c) identifying progeny generated in (b) that exhibit a sensitizer gene-specific antiproliferation phenotype in the limited portion of the target tissue; and
    (d) identifying as an anti cell proliferation drug target, an interactor gene from a progeny identified in (c) that when mutated or underexpressed, results in the sensitizer gene-specific antiproliferation phenotype.

2. The method of claim 1 wherein the gene is an ortholog of a human tumor suppressor gene.

3. The method of claim 2 further comprising:
    (e) identifying a human ortholog of the interactor gene.

4. The method of claim 2 wherein the human tumor suppressor gene is selected from the group consisting of BRCA1, Rb, p16, p53, VHL, and Beta-Catenin.

5. The method of claim 1 wherein Drosophila is used and altered sensitizer gene expression is under the control of a regulatory element from a gene selected from the group consisting of eyeless, sevenless, mirror, glass, dpp, and vestigal.

6. The method of claim 1 wherein *C. elegans* is used and altered sensitizer gene expression is under the control of a regulatory element from a gene selected from the group consisting of lin-31, hlh-1, and myo-2.

7. The method of claim 1 wherein the marker gene is selected from the group consisting of white, rosy, ncl-1, GFP, and LacZ.

8. The method of claim 1 wherein the gene is a tumor suppressor gene and a Drosophila is used that is created by knocking out an endogenous tumor suppressor gene in all tissues, and replacing tumor suppressor gene function with a rescue construct that allows expression of the sensitizer gene in all tissues except the limited portion of the target tissue.

9. The method of claim 1 wherein the rescue construct comprises:
from 5' to 3': a first insertion sequence, and a first recombination target sequence; from 3' to 5': a second insertion sequence, and a second recombination target sequence; and
in any order between the first and second recombination target sequences; the sensitizer gene, a marker gene, and a gene comprising a sequence encoding a site-specific recombinase operably linked to a promoter active in the target tissue;
such that, upon introduction into the Drosophila, the recombinase is expressed in the limited portion of the target tissue and excises the genes between the first and second recombination target sequences.

10. The method of claim 9 wherein the recombination target sequences comprise FRT direct repeat sequences and the site-specific recombinase is FLP recombinase.

11. The method of claim 1 wherein expression of two or more sensitizer genes is altered simultaneously.

12. The method of claim 1 wherein step (b) is performed using a large-scale genetic modifier screen format wherein random mutations are introduced into the putative interactor genes.

13. The method of claim 1 wherein in step (b) expression of putatative interactor genes is caused by using a method selected from the group consisting of transposon mutagenesis and RNAi.

14. The method of claim 1 wherein the gene is an ortholog of a human oncogene.

15. The method of claim 1 wherein Drosophila is used and the gene is selected from the group consisting of Rb, ras, lats, and p53.

16. The method of claim 1 wherein *C. elegans* is used and the gene is selected from the group consisting of ras, cdc25, cyclin E, cullin, Rb, cdk, and p21.

17. The method of claim 1 wherein Drosophila is used and the target tissue is selected from the group consisting of eyes and wings.

18. The method of claim 1 wherein *C. elegans* is used and the target tissue is selected from the group consisting of vulval, muscle, and nerve tissue.

19. The method of claim 1 wherein the altered expression is caused by overexpression of the gene.

20. The method of claim 19 wherein the overexpression of the gene is caused by introducing a transformation construct into the Drosophila or *C. elegans* that comprises:
from 5' to 3': a first insertion sequence, a regulatory sequence, a first recombination target sequence, and a transcription termination sequence;
from 3' to 5': a second insertion sequence, an inactive sensitizer gene, and a second recombination target sequence; and
in any order between the transcription termination sequence and the second recombination sequence: a marker gene and a gene comprising a sequence encoding site-specific recombinase operably linked to a promoter active in the target tissue;
such that, upon introduction into the Drosophila or *C. elegans*, the recombinase is expressed in the target tissue and excises the genes between the first and second recombination target sequences thereby juxtaposing the regulatory sequence and the sensitizer gene such that the sensitizer gene becomes activated.

21. The method of claim 20 wherein the gene is an oncogene.

22. The method of claim 20 wherein the gene is a dominant negative mutant of an endogenous tumor suppressor gene such that overexpression of the sensitizer gene blocks the function of the endogenous tumor suppressor gene product.

23. The method of claim 20 wherein Drosophila is used, and the transformation construct comprises a mirror enhancer flanked by two promoters, a first promoter that drives expression of the marker gene, and a second promoter that drives expression of 2 sensitizer gene.

* * * * *